US006306607B2

(12) United States Patent
Williams

(10) Patent No.: US 6,306,607 B2
(45) Date of Patent: *Oct. 23, 2001

(54) HETEROGENEOUS ASSAY FOR PYROPHOSPHATE

(75) Inventor: John G. K. Williams, Lincoln, NE (US)

(73) Assignee: LI-COR, Inc., Lincoln, NE (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/816,720

(22) Filed: Mar. 21, 2001

Related U.S. Application Data

(63) Continuation of application No. 09/460,304, filed on Dec. 13, 1999, now Pat. No. 6,232,075
(60) Provisional application No. 60/115,496, filed on Jan. 11, 1999, and provisional application No. 60/112,078, filed on Dec. 14, 1998.

(51) Int. Cl.[7] .................... C12Q 1/68; G01N 33/53; G01N 33/566
(52) U.S. Cl. .................... 435/6; 435/7; 424/12; 436/501; 935/77; 935/78
(58) Field of Search ............... 435/6, 7; 424/12; 436/501; 935/77, 78

(56) References Cited

U.S. PATENT DOCUMENTS

| 4,318,981 | * | 3/1982 | Burd et al. ................ 435/7 |
| 4,415,732 | | 11/1983 | Caruthers et al. .......... 536/27 |
| 4,458,066 | | 7/1984 | Caruthers et al. .......... 536/27 |
| 4,863,849 | | 9/1989 | Melamede ................ 435/6 |
| 4,962,037 | | 10/1990 | Jett et al. ................ 435/6 |
| 4,996,143 | | 2/1991 | Heller et al. .............. 435/6 |
| 5,013,831 | | 5/1991 | Stavrianopoulos ......... 536/27 |
| 5,047,519 | | 9/1991 | Hobbs, Jr. et al. ......... 536/27 |
| 5,241,060 | | 8/1993 | Engelhardt et al. ........ 536/27 |
| 5,260,433 | | 11/1993 | Engelhardt et al. ........ 536/23.1 |
| 5,332,666 | | 7/1994 | Prober et al. ............. 435/91.5 |
| 5,405,747 | | 4/1995 | Jett et al. ................ 435/6 |
| 5,608,063 | | 3/1997 | Hobbs, Jr. et al. ......... 544/244 |
| 5,635,608 | | 6/1997 | Haugland et al. .......... 536/1.11 |
| 5,714,330 | | 2/1998 | Brenner et al. ............ 435/6 |
| 5,723,591 | | 3/1998 | Livak et al. .............. 536/22.1 |
| 5,800,996 | | 9/1998 | Lee et al. ................ 435/6 |
| 5,846,737 | | 12/1998 | Kang .................... 435/7.1 |
| 5,863,727 | | 1/1999 | Lee et al. ................ 435/6 |
| 5,866,336 | | 2/1999 | Nazarenko et al. ......... 435/6 |
| 5,872,243 | | 2/1999 | Gee et al. ................ 536/26.23 |

FOREIGN PATENT DOCUMENTS 272007  3/1992  (EP) .................... C09B/11/24

OTHER PUBLICATIONS

Agrawal et al., "Site–Specific Functionalization of Oligodeoxynucleotides For Non–Radioactive Labelling," *Tetrahedron Letters*, 31:1543–1546 (1990).

Ambrose et al., "Single–Molecule Detection With Total Internal Reflection Excitation: Comparing Signal–to–Background and Total Signals in Different Geometries," *Cytometry*, 36:224–231 (1991).

(List continued on next page.)

*Primary Examiner*—Jeffrey Fredman
*Assistant Examiner*—Arun Kr. Chakrabarti
(74) *Attorney, Agent, or Firm*—Townsend and Townsend and Crew LLP

(57) ABSTRACT

Nucleotide triphosphate probes containing a fluorophore attached to the γ-phosphate and a quencher moiety sufficiently proximal to the fluorophore moiety for use in pyrophosphate detection assays are disclosed. These probes exhibit distinguishable fluorescence characteristics when the fluorophore is attached to the nucleotide through the γ-phosphate and when it is unattached to the nucleotide. The present invention also provides kits and integrated systems for practicing the assays described herein.

25 Claims, 11 Drawing Sheets

OTHER PUBLICATIONS

Araki et al., "Allosteric regulation of a ribozyme activity through ligand–induced conformational change," *Nucleic Acids Res.*, 26:3379–3384 (1998).

V.W. Armstrong and F. Eckstein, "Interaction of Substrate Analogues with *Escherichia coli* DNA–Dependent RNA Polymerase," *Eur. J. Biochem.*, 70:30–38 (1976).

Asanov et al., "Regenerable Biosensor Platform: A Total Internal Reflection Fluorescence Cell with Electrochemical Control," *Anal. Chem.* 70:1156–1163 (1998).

Bergstrom et al., "Palladium–Mediated Coupling between Organic Disulfides and Nucleic Acid Constituents," *JACS*, 111:374–375 (1989).

Castro, A. and Williams, J.G.K. "Single–Molecule Detection of Specific Nucleic Acid Sequences in Unamplified Genomic DNA," *Anal. Chem.* 69:3915–3920 (1997).

Church, G.M. and Kieffer–Higgins, S. "Multiplex DNA Sequencing," *Science*, 240:185–188 (1988).

Davis et al., "Rapid DNA Sequencing Based Upon Single Molecule Detection," *GATA* 8(1):1–7 (1991).

Eckstein, F., and Thompson, J.B., "Phosphate Analogs for the Study DNA Polymerases," *Methods in Enzymology*, 262:189–217 (1995).

Edman et al., "Conformational transitions monitored for single molecules in solution," *Proc. Natl. Acad. Sci. USA*, 93:6710–6715 (1996).

Fleischmann et al., "Whole–Genome Random Sequencing and Assembly of *Haemophilus influenzae* Rd," *Science*, 269:496–511 (1995).

Garcia, A.M., "Determination of Ion Permeability by Fluorescence Quenching," *Meth. Enzymol.*, 207:501–511 (1992).

Gebeyehu et al., "Novel biotinylated nucleotide—analogs for labeling and colorimetric detection of DNA," *Nucleic Acids Research*, 15:4513–4535 (1987).

Gibson, K.J. and Benkovic, S.J., "Synthesis and application of derivatizable oligonucleotides," *Nucleic Acids Research*, 15: 6455–6467 (1987).

Giusti et al., "Synthesis and Characterization of 5'–Fluorescent –dye–labeled Oligonucleotides," *PCR Methods and Applications*, 2: 223–227 (1993).

Goody et al., "The Enzymatic Synthesis of Thiophosphate Analogs of Nucleotides," *Biochem. Biophys. Acta.*, 276:155–161 (1972).

Grachev, M.A. and Zaychikov, E.F., "ATP γ–Anilidate; A Substrate of DNA–Dependent RNA–Polymerase of *Escherichia Coli,*" *FEBS Lett.*, 49:163–166 (1974).

Griffin, et al., "Specific Covalent Labeling of Recombinant Protein Molecules Inside Live Cells," *Science*, 281:269–272 (1998).

Gupta et al., "A general method for the synthesis of 3'–sulfhydryl and phosphate group containing oligonucleotides," *Nucleic Acids Research*, 19:3019–3025 (1991).

Gyllensten, U. and Allen, M., "PCR–based HLA Class II Typing," *PCR Methods and Applications*, 1: 91–98 (1991).

Haralambidis et al., "Preparation of base–modified nucleosides suitable for non–radioactive label attachment and their incorporation into synthetic oligodeoxyribonucleotides," *Nucleic Acids Research*, 15: 4856–4876 (1987).

Hobbs, F.W., "Palladium–Catalyzed Synthesis of Alkynylamino Nucleosides. A Universal Linker for Nucleic Acids," *J. Org. Chem.*, 54: 3420–3422 (1989).

Hunkapiller et al., "Large–Scale and Automated DNA Sequence Determination," *Science*, 254: 59–67 (1991).

Hyman, E.D., "A New Method of Sequencing DNA," *Analytical Biochemistry* 174:423–436 (1988).

Jett et al., "High–Speed DNA Sequencing: An Approach Based Upon Fluorescence Detection of Single Molecules," *J. Biomol. Struct. Dyn.* 7:301–309 (1989).

Kinjo, M. and Rigler, R., "Ultrasensitive hybridization analysis using fluorescence correlation spectroscopy," *Nucleic Acids Res.*, 23:1795–1799 (1995).

Köster et al., "A strategy for rapid and efficient DNA sequencing by mass spectrometry," *Nature Biotechnology*, 14:1123–1128 (1996).

Laws, W.R. and Contino, P.B., "Fluorescence Quenching Studies: Analysis of Nonlinear Stern—Volmer Data," *Meth. Enzymol.*, 210:448–463 (1992).

Li, Y. and Glazer, A.N., "Design, Synthesis, and Spectroscopic Properties of Peptide–Bridged Fluorescence Energy–Transfer Cassettes," *Bioconjugate Chem.*, 10:241–245 (1999).

Marshall, P.N., "Rules for the visible absorption spectra of halogenated Fluorescein dyes," *Histochemical J.*, 7:299–303 (1975).

Maxam, A.M. and Gilbert, W.G., "A new method for sequencing DNA," *Proc. Natl. Acad. Sci. USA*, 74: 560–564 (1977).

Narasimhan, K. and Wingard Jr., L.B., "ρ–Benzoquinone activation of metal oxide electrodes for attachment of enzymes," *Enzyme Microb. Technol.*7:283–286 (1985).

Nelson et al., "A Convenient Preparation of a New C–5 Biotinylated dUTP Derivative," *Nucleosides and Nucleotides*, 5(3):233–241 (1986).

Nelson et al., "Bifunctional oligonucleotide probes synthesized using a novel CPG support are able to detect single base pair mutations," *Nucleic Acids Research*, 17:7187–7194 (1989).

Nie, et al., "Probing Individual Molecules with Confocal Fluorescence Microscopy," *Science* 266:1018–1021 (1994).

Nie et al., "Real–Time Detection of Single Molecules in Solution by Confocal Fluorescence Microscopy," *Anal. Chem.* 67:2849–2837 (1995).

Paris et al., "Probing DNA sequences in solution with a monomer—excimer fluorescence color change," *Nucleic Acids Res.*, 26:3789–2393 (1998).

Ronaghi et al., "Sequencing Method Based on Real–Time Pyrophosphate," *Science*, 281:363–365 (1998).

Rozinov, M.N. and Nolan, G.P., "Evolution of peptides that modulate the spectral qualities of bound, small–molecule fluorophores," *Chemistry & Biology*, 5:713–728 (1998).

Sanger et al., "DNA sequencing with chain–terminating inhibitors," *Proc. Natl. Acad. Sci. USA*, 74: 5463–5467 (1977).

Sato, et al., "Bimane conjugates of 5–halogenouridylic acids as fluorogenic substrates for phosphodiesterase I", *J. Chem. Research (S)*, 1:390–391 (1994).

Schecker et al., "Flow–based continuous DNA sequencing via single molecule detection of enzymatically cleaved fluorescent nucleotides", *Proc. SPIE–Int. Soc. Opt. Eng.* 2386:4–12 (1995).

Schmidt et al. "Imaging of single molecule diffusion," *Proc. Natl. Acad. Sci. USA* 93,2926–2929 (1996).

Service, R.F., "Borrowing from biology to power the petite", *Science*, 283:27 (1999).

Smagowicz et al., "Properties of $P^3$ Esters of Nucleoside Triphosphates as Substrates for RNA Polymerase from *Escherichia coli,* " *Biochem.*, 20:5538–5546 (1981).

Steitz, T.A., "A mechanism for all polymerases," *Nature*, 391:231–232 (1998).

Tokunaga et al., "Single molecule imaging of fluorophores and enzymatic reactions achieved by objective–type total internal reflection fluorescence microscopy", *Biochem. and Biophys. Res. Comm.* 235:47–53 (1997).

Tyagi et al., "Multicolor molecular beacons for allele discrimination," *Nature Biotechnol.*, 16:49–53 (1998).

Velculescu et al., "Serial Analysis of Gene Expression," *Science*, 270:484–487 (1995).

Wang et al., "Design and Synthesis of New Fluorogenic HIV Protease Substrates Based On Resonance Energy Transfer," *Tetrahedron Lett.* 31:6493–6496 (1990).

Weissleder et al., "In vivo imaging of tumors with protease–activated near–infrared fluorescent probes," *Nature Biotechnol.*, 17:375–378 (1999).

Wu et al., "Synthesis and Properties of Adenosine–5'–triphosphoro–γ–1–(5–sulfonic acid)naphthyl Ethylamidate: A Fluorescent Nucleotide Substrate for DNA–Dependent RNA Polymerase from *Escherichia coli,*" *Arch. Biochem. Biophys.*, 246:564–567 (1986).

Wu, L., and Curran, J.F., "An allosteric synthetic DNA," *Nucleic Acids Res.*, 1512–1516 (1999).

Xu, X.N. and Yeung, E.S., "Long–Range Electrostatic Trapping of Single–Protein Molecules at a Liquid–Solid Interface," *Science*, 251:1650–1653 (1998).

Yarbrough, et al., "Synthesis and properties of fluorescent nucleotide substrates for DNA–dependent RNA polymerases," *JBC*, 254:12069–12073 (1979).

Zuckermann et al., "Efficient methods for attachment of thiol specific probes to the 3'–ends of synthetic oligodeoxyribonucleotides," *Nucleic Acids Research*, 15: 5305–5321 (1987).

Livak, et al., Oligonucleotides with Fluorescent Dyes at Opposite Ends Provide a Quenched Probe System Useful for Detecting PCR Product and Nucleic Acid Hybridization, *PCR Methods and Applications*, Cold Spring Harbor Laboratory Press. 4:357–362 (1995).

\* cited by examiner

FIGURE 1
A. dNTP Incorporation
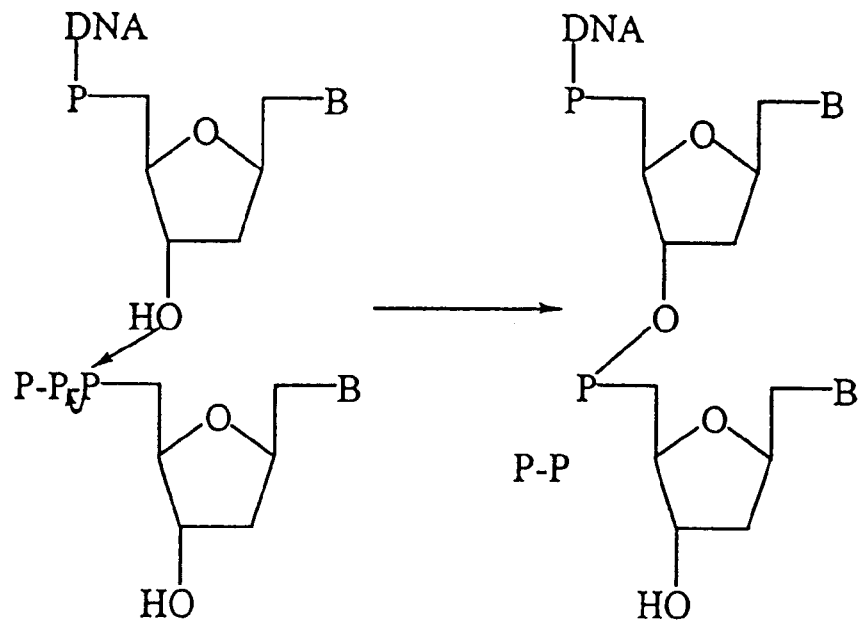
B. Quenched dNTP Incorporation
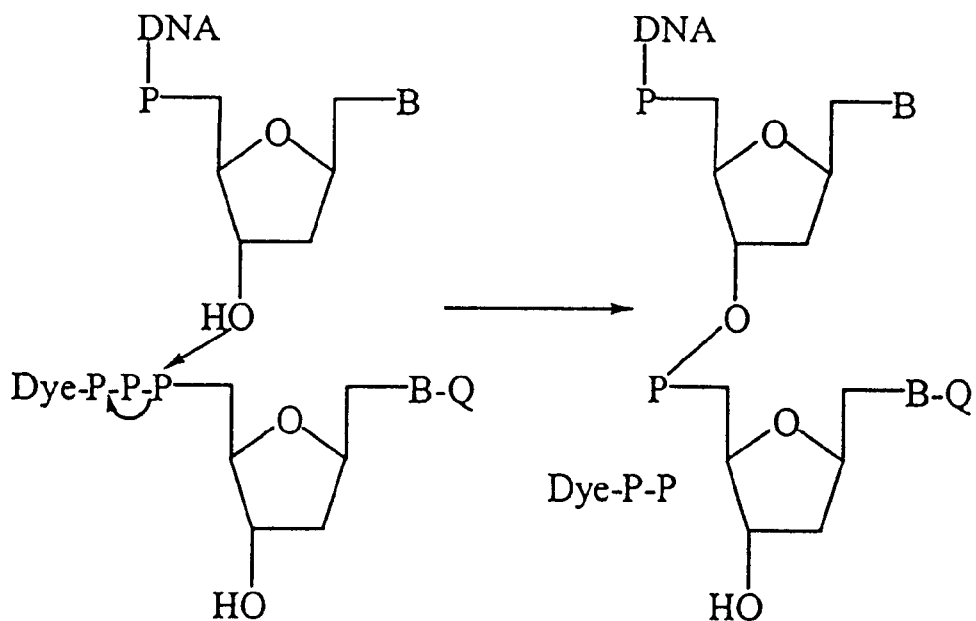

Figure 2
A.
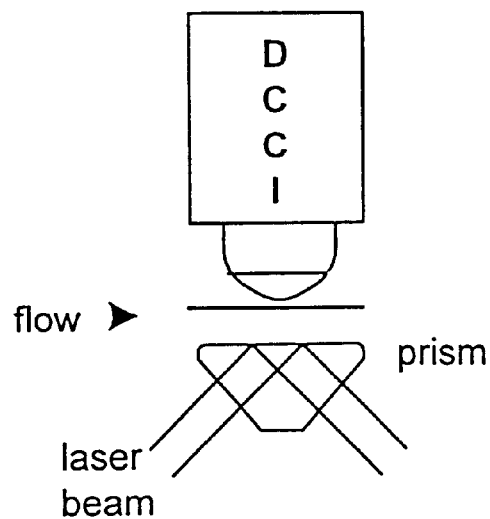
B.
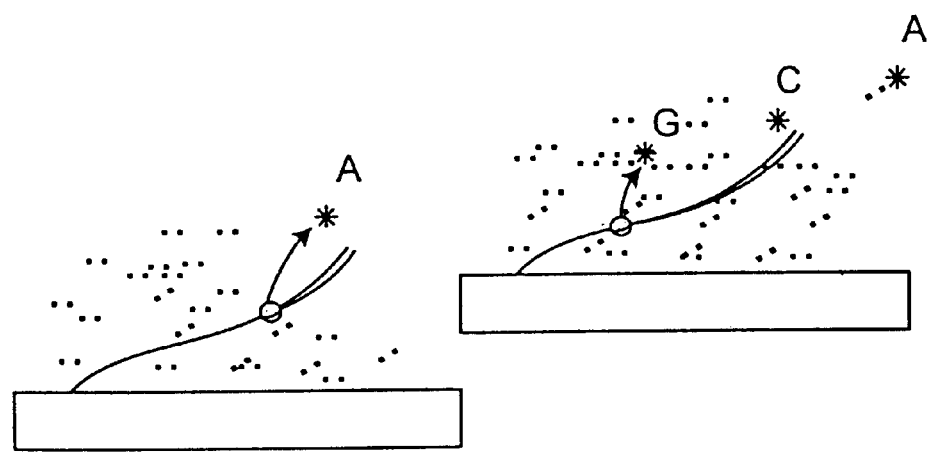

Synthesis of Iodoacetamidyl IRD 38

HETEROGENEOUS ASSAY FOR PYROPHOSPHATE

CROSS-REFERENCES TO RELATED APPLICATIONS

The present application is a continuation of U.S. patent application Ser. No. 09/460,304, U.S. Pat. No. 6,232,075, filed Dec. 13, 1999, allowed, which claims priority to U.S. Provisional Patent Application Serial No. 60/112,078, filed Dec. 14, 1998, and Ser. No. 60/115,496, filed Jan. 11, 1999, the disclosures of which are hereby incorporated by reference in their entirely for all purposes.

FIELD OF THE INVENTION

This invention relates generally to a heterogeneous assay, and in particular, to assay methods using fluorescent nucleotide triphosphates having a fluorophore moiety attached to the γ-phosphate that are especially useful for pyrophosphate detection.

BACKGROUND OF THE INVENTION

The primary sequences of nucleic acids are crucial for understanding the function and control of genes and for applying many of the basic techniques of molecular biology. The ability to do rapid and reliable DNA sequencing is therefore a very important technology. The DNA sequence is an important tool in genomic analysis as well as other applications, such as genetic identification, forensic analysis, genetic counseling, medical diagnostics, etc. With respect to the area of medical diagnostic sequencing, disorders, susceptibilities to disorders, and prognoses of disease conditions, can be correlated with the presence of particular DNA sequences, or the degree of variation (or mutation) in DNA sequences, at one or more genetic loci. Examples of such phenomena include human leukocyte antigen (HLA) typing, cystic fibrosis, tumor progression and heterogeneity, p53 proto-oncogene mutations and ras proto-oncogene mutations (see, Gyllensten et al., PCR Methods and Applications, 1: 91–98 (1991); U.S. Pat. No. 5,578,443, issued to Santamaria et al.; and U.S. Pat. No. 5,776,677, issued to Tsui et al.).

Various approaches to DNA sequencing exist. The dideoxy chain termination method serves as the basis for all currently available automated DNA sequencing machines. (see, Sanger et al., *Proc. Natl. Acad. Sci.,* 74: 5463–5467 (1977); Church et al., *Science,* 240: 185–188 (1988); and Hunkapiller et al., *Science,* 254: 59–67 (1991)). Other methods include the chemical degradation method, (see, Maxam et al., *Proc. Natl. Acad. Sci.,* 74: 560–564 (1977), whole-genome approaches (see, Fleischmann et al., *Science,* 269, 496 (1995)), expressed sequence tag sequencing (see, Velculescu et al., *Science,* 270, (1995)), array methods based on sequencing by hybridization (see, Koster et al., *Nature Biotechnology,* 14, 1123 (1996)), and single molecule sequencing (SMS) (see, Jett et al., *J. Biomol. Struct. Dyn.* 7, 301 (1989) and Schecker et al., Proc. SPIE-*Int. Soc. Opt. Eng.* 2386, 4 (1995)).

Fluorescent dyes can be used in a variety of these DNA sequencing techniques. A fluorophore moiety or dye is a molecule capable of generating a fluorescence signal. A quencher moiety is a molecule capable of absorbing the fluorescence energy of an excited fluorophore, thereby quenching the fluorescence signal that would otherwise be released from the excited fluorophore. In order for a quencher to quench an excited fluorophore, the quencher moiety must be within a minimum quenching distance of the excited fluorophore moiety at some time prior to the fluorophore releasing the stored fluorescence energy.

Fluorophore-quencher pairs have been incorporated into oligonucleotide probes in order to monitor biological events based on the fluorophore and quencher being separated or brought within a minimum quenching distance of each other. For example, probes have been developed wherein the intensity of the fluorescence increases due to the separation of the fluorophore-quencher pair. Probes have also been developed which lose their fluorescence because the quencher is brought into proximity with the fluorophore. These fluorophore-quencher pairs have been used to monitor hybridization assays and nucleic acid amplification reactions, especially polymerase chain reactions (PCR), by monitoring either the appearance or disappearance of the fluorescence signal generated by the fluorophore molecule.

The decreased fluorescence of a fluorophore moiety by collision or direct interaction with a quencher is due mainly to a transfer of energy from the fluorophore in the excited state to the quencher. The extent of quenching depends on the concentration of quencher and is described by the Stern-Volmer relationship:

$$F_o/F = 1 + K_{sv}[Q]$$

wherein $F_o$ and $F$ correspond to the fluorescence in the absence and presence of quencher, respectively, and $[Q]$ is the quencher concentration. A plot of $F_o/F$ versus $[Q]$ yields a straight line with a slope corresponding to the Stern-Volmer constant, $K_{sv}$. The foregoing equation takes into account the dynamic and collisional quenching which is the dominant component of the quenching reaction. However, deviations from linearity are observed when contributions by static quenching becomes significant, or when the quenching is not efficient (see, A. M. Garcia, *Methods in Enzymology,* 207, 501–511 (1992)).

In general, fluorophore moieties preferably have a high quantum yield and a large extinction coefficient so that the dye can be used to detect small quantities of the component being detected. Fluorophore moieties preferably have a large Stokes shift (i.e., the difference between the wavelength at which the dye has maximum absorbance and the wavelength at which the dye has maximum emission) so that the fluorescent emission is readily distinguished from the light source used to excite the dye.

One class of fluorescent dyes which has been developed is the energy transfer fluorescent dyes. For instance, U.S. Pat. Nos. 5,800,996, and 5,863,727, issued to Lee et al., disclose donor and acceptor energy fluorescent dyes and linkers useful for DNA sequencing. In energy transfer fluorescent dyes, the acceptor molecule is a fluorophore which is excited at the wavelength of light emitted by the excited donor molecule. When excited, the donor dye transmits its energy to the acceptor dye. Therefore, emission from the donor is not observed. The emission from the donor dye excites the acceptor dye, and causes the acceptor dye to emit at its characteristic wavelength (i.e., a wavelength different from that of the donor dye, therefore observed as a color different from that of the donor). The advantage of this mechanism is twofold; the emission from the acceptor dye is more intense than that from the donor dye alone (see, Li et al., *Bioconjugate Chem.,* 10: 242–245, (1999)) and attachment of acceptor dyes with differing emission spectra allows differentiation among molecules by fluorescence using a single excitation wavelength.

Nucleotide triphosphates having a fluorophore moiety attached to the γ-phosphate are of interest as this modification still allows the modified NTPs to be enzyme substrates. For instance, Felicia et al., describe the synthesis and spectral properties of a "always-on" fluorescent ATP analog, adenosine-5'-triphosphoro-γ-1-(5-sulfonic acid)-naphthyl ethylamindate (γ-1,5-EDANS)ATP. The analog is a good substrate for *E. Coli* RNA polymerase and can be used to initiate the RNA chain. The ATP analog is incorporated into the RNA synthesized and is a good probe for studies of nucleotide-protein interactions, active site mapping and other ATP-utilizing biological systems (see, Felicia et al., *Arch. Biochem Biophys.*, 246: 564–571 (1986)).

In addition, Sato et al., disclose a homogeneous enzyme assay that uses a fluorophore moiety (bimane) attached to the γ-phosphate group of the nucleotide and a quencher moiety attached to the 5-position of uracil. The quencher moiety is in the form of a halogen, bound to the C-5 position of the pyrimidine. The quenching that is effected by this combination is eliminated by cleavage of the phosphate bond by the phosphodiesterase enzyme. The halogen quencher used in the assay is very inefficient producing only about a two fold decrease in fluorescent efficiency.

A need currently exists for effective nucleotide triphosphate molecules containing a fluorophore and a quencher for use in pyrophosphate detection assays. Accordingly, a need exists for assays using probes which exhibit distinguishable fluorescence characteristics when a fluorophore is attached to the nucleotide through the γ-phosphate and when it is unattached to the nucleotide. A further need exists for assays using probes wherein the fluorophore and a quencher are positioned on the probe such that the quencher moiety can effectively quench the fluorescence of the fluorophore moiety. These and further objectives are provided by the methods and probes of the present invention.

SUMMARY OF THE INVENTION

A need currently exists for effective nucleotide triphosphate molecules containing a fluorophore and a quencher for use in pyrophosphate detection assays. Pyrophosphate detection is useful for monitoring a number of enzymatic reaction mechanisms such as nucleic acid polymerase reactions. As such, in certain aspects, the present invention provides a heterogeneous assay method for detecting pyrophosphate cleavage, the components of the assay comprising a labeled NTP, a target nucleic acid, a primer nucleic acid and a polymerase, the method comprising:

(a) flowing the labeled nucleotide triphosphate (NTP) having a γ-phosphate with a fluorophore moiety attached thereto and a quencher moiety sufficiently proximal to the fluorophore moiety to prevent fluorescence of the fluorophore moiety, past an immobilized component selected from the group consisting of the polymerase and the target nucleic acid;

(b) incorporating the labeled NTP on the primer strand hybridized to the target nucleic acid using the polymerase and releasing the γ-phosphate with the fluorophore moiety attached thereto; and (c) detecting the fluorescent moiety thereby detecting pyrophosphate cleavage.

Preferably, in the methods of the present invention, the enzyme is immobilized on a solid support and the nucleotide triphosphates comprise dATP, dCTP, dGTP, dTTP, dUTP, ATP, CTP, GTP, UTP and mixtures thereof. The detection of the fluorescent moieties is preferably accomplished using single molecule detection with for example, a charge couple device (CCD) camera.

In another aspect, the present invention provides a nucleotide triphosphate (NTP) probe, comprising: a NTP having a γ-phosphate with a fluorophore moiety attached thereto; a quencher moiety sufficiently proximal to the fluorophore moiety to prevent fluorescence of the fluorophore moiety; wherein the fluorophore moiety exists quenched with at least about a 5 fold quenching efficiency when the γ-phosphate is attached to the NTP and unquenched when the γ-phosphate is detached from the NTP. In preferred aspects, the quencher moiety is attached to the nucleobase.

In yet another aspect, the present invention provides kits and integrated systems for practicing the assays described herein. In certain aspects, the present invention provides a kit for assaying pyrophosphate cleavage, comprising: (a) a plurality of NTPs each having a γ-phosphate with a distinguishing fluorophore moiety attached thereto and each having a quencher moiety sufficiently proximal to the distinguishing fluorophore moiety to prevent fluorescence of the distinguishing fluorophore moiety; wherein the distinguishing fluorophore moiety exists quenched with at least about a 5 fold quenching efficiency when the γ-phosphate is attached to each of the plurality of dNTP moieties and each is unquenched when the γ-phosphate is detached from each of the plurality of dNTP moieties; and (b) a polymerase. Preferably, the polymerase is immobilized on a solid support.

These and other aspects and advantages will become more apparent when read with the accompanying figures and the detailed description that follows.

BRIEF DESCRIPTION OF THE DRAWINGS

FIG. 1 Panel A illustrates pyrophosphate cleavage with a polymerase; Panel B illustrates an embodiment of the present invention.

DEFINITIONS

Figure 2:
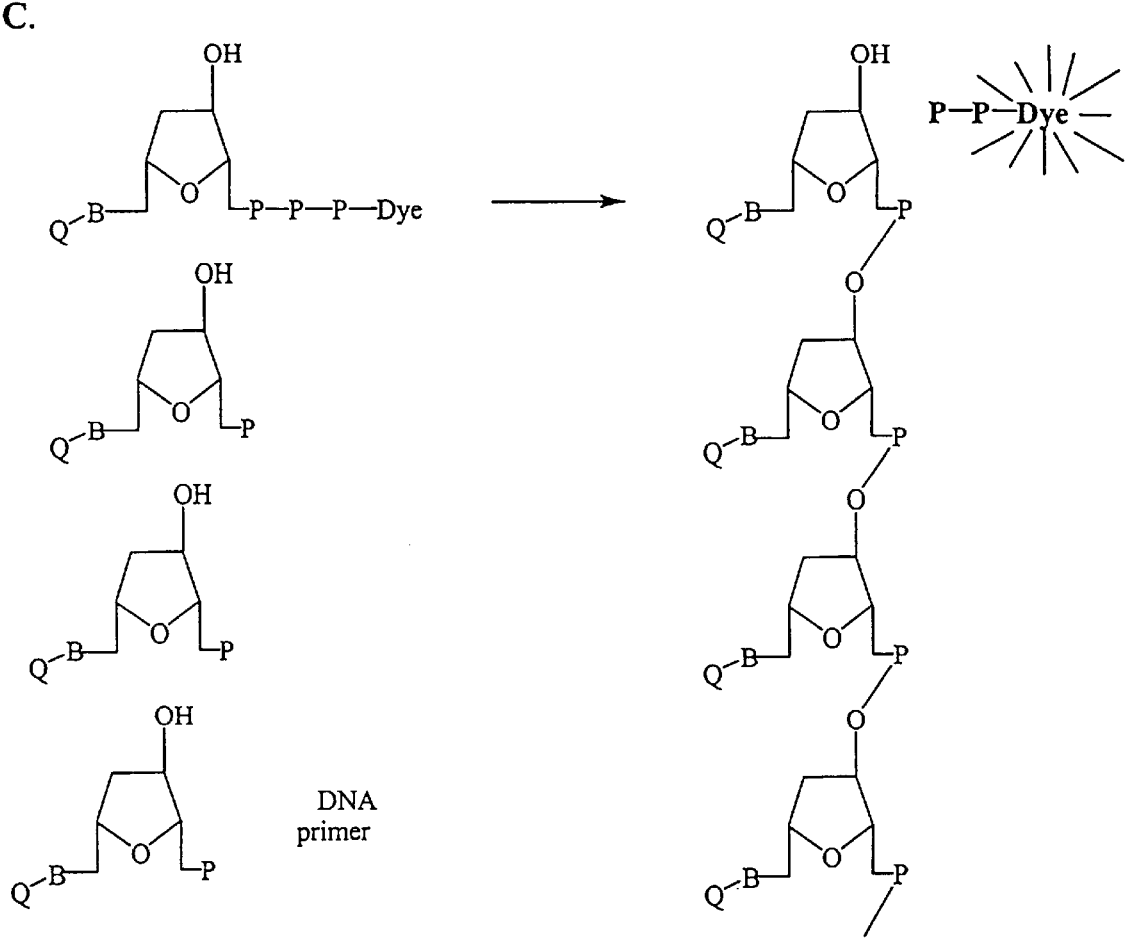
FIG. 2 Panel A illustrates an optical set of the present invention; Panel B illustrates a single molecule sequencing embodiment of the present invention; Panel C illustrates an embodiment of the present invention.

The term "heterogeneous" assay as used herein refers to an assay method wherein at least one of the reactants in the assay mixture is attached to a solid phase, such as a solid support.

The term "oligonucleotide" as used herein includes linear oligomers of nucleotides or analogs thereof, including deoxyribonucleosides, ribonucleosides, and the like. Usually, oligonucleotides range in size from a few monomeric units, e.g . 3–4, to several hundreds of monomeric units. Whenever an oligonucleotide is represented by a sequence of letters, such as "ATGCCTG," it will be understood that the nucleotides are in 5'–3' order from left to right and that "A" denotes deoxyadenosine, "C" denotes deoxycytidine, "G" denotes deoxyguanosine, and "T" denotes thymidine, unless otherwise noted.

The term "nucleoside" as used herein refers to a compound consisting of a purine, deazapurine, or pyrimidine nucleoside base, e.g., adenine, guanine, cytosine, uracil, thymine, deazaadenine, deazaguanosine, and the like, linked to a pentose at the 1' position, including 2'-deoxy and 2'-hydroxyl forms, e.g., as described in Komberg and Baker, *DNA Replication,* 2nd Ed. (Freeman, San Francisco, 1992).

The term "nucleotide" as used herein refers to a phosphate ester of a nucleoside, e.g., mono, di and triphosphate esters, wherein the most common site of esterification is the hydroxyl group attached to the C-5 position of the pentose. Nucleosides also include, but are not limited to, synthetic nucleosides having modified base moieties and/or modified sugar moieties, e.g. described generally by Scheit, Nucleotide Analogs (John Wiley, N.Y., 1980). Suitable NTPs include both naturally occurring and synthetic nucleotide triphosphates, and are not limited to, ATP, dATP, CTP, dCTP, GTP, dGTP, TTP, dTTP, UTP and dUTP. Preferably, the nucleotide triphosphates used in the methods of the present invention are selected from the group of dATP, dCTP, dGTP, dTTP, dUTP and mixtures thereof.

The term "primer" refers to a linear oligonucleotide which specifically anneals to a unique polynucleotide sequence and allows for amplification of that unique polynucleotide sequence.

The phrase "sequence determination" or "determining a nucleotide sequence" in reference to polynucleotides includes determination of partial as well as full sequence information of the polynucleotide. That is, the term includes sequence comparisons, fingerprinting, and like levels of information about a target polynucleotide, or oligonucleotide, as well as the express identification and ordering of nucleosides, usually each nucleoside, in a target polynucleotide. The term also includes the determination of the identification, ordering, and locations of one, two, or three of the four types of nucleotides within a target polynucleotide.

The term "solid-support" refers to a material in the solid-phase that interacts with reagents in the liquid phase by heterogeneous reactions. Solid-supports can be derivatized with proteins such as enzymes, peptides, oligonucleotides and polynucleotides by covalent or non-covalent bonding through one or more attachment sites, thereby "immobilizing" the protein or nucleic acid to the solid-support.

The phrase "target nucleic acid" or "target polynucleotide" refers to a nucleic acid or polynucleotide whose sequence identity or ordering or location of nucleosides is to be determined using methods described herein.

DETAILED DESCRIPTION OF THE INVENTION AND PREFERRED EMBODIMENTS

I. Methods

A. Pyrophosphate Cleavage

In certain embodiments, the present invention provides a heterogeneous assay for the detection of pyrophosphate. The detection of pyrophosphate is advantageous in a number of biological reactions. For example, in a DNA polymerase reaction, wherein the polymerase selects a single DNA molecule from solution and thereafter incorporates the nucleotide at the 3'-end of a primer strand, the natural consequence of such incorporation is the release of pyrophosphate. If the assay solution comprises the four deoxynucleotide triphosphates, each dNTP labeled with a different color of fluorescent dye attached to the γ-phosphate, it is then possible to sequentially record the activity of the polymerase operating on a target DNA. The nucleotide sequence of the target DNA can thereafter be read directly from the order of released dyes attached to the pyrophosphate.

As such, the present invention provides a heterogeneous assay method for detecting pyrophosphate cleavage, the components of the assay comprising a labeled NTP, a target nucleic acid, a primer nucleic acid and a polymerase, the method comprising: (a) flowing the labeled nucleotide triphosphate (NTP) having a γ-phosphate with a fluorophore moiety attached thereto and a quencher moiety sufficiently proximal to the fluorophore moiety to prevent fluorescence of the fluorophore moiety, past an immobilized component selected from the group consisting of the polymerase and the target nucleic acid; (b) incorporating the NTP on a primer strand hybridized to the target nucleic acid using an enzyme and releasing the γ-phosphate with the fluorophore moiety attached thereto; and (c) detecting the fluorescent moiety thereby detecting pyrophosphate cleavage. In the heterogeneous assay of the present invention, either the polymerase or the target nucleic acid is attached to a solid phase, such as a solid support. Preferably, in the methods of the present invention, the polymerase is immobilized on a solid support.

In certain aspects, the polymerase is a DNA polymerase such as DNA polymerase I, II or III. In other aspects, suitable polymerases include, but are not limited to, a DNA dependent RNA polymerase and reverse transcriptase such as an HIV reverse transcriptase. Specific examples include, but are not limited to, T7 DNA polymerase, T5 DNA polymerase, *E. Coli* DNA polymerase I, T4 DNA polymerase, T7 RNA polymerase and Taq DNA polymerase. Those of skill in the art will know of other enzymes or polymerases suitable for use in the present invention. In certain aspects, the polymerase is bathed in a flowing solution comprising: unlabeled, single-stranded DNA fragments hybridized to an oligonucleotide primer and a mixture of NTPs.

In certain aspects of the present invention, a labeled nucleotide triphosphate (NTP) having a γ-phosphate with a fluorophore moiety attached thereto is incorporated into a polynucleotide chain. As illustrated in FIG. 1A, dNTP incorporation into a growing oligonucleotide by a DNA polymerase results in pyrophosphate cleavage. In this reaction, the phosphate ester bond between the α and β phosphates of the incorporated nucleotide is cleaved by the DNA polymerase, and the β-γ-diphosphate (pyrophosphate) is released in solution. As used herein, the term pyrophosphate also includes substitution of any of the oxygen atoms of the pyrophosphate group with a nitrogen or a sulfur atom or combinations thereof to generate thiopyrophosphate, dithiopyrophosphate, etc.

As shown in FIG. 1B, in compounds of the present invention wherein a fluorophore is attached to the γ-phosphate, the fluorophore is released from the nucleotide along with the pyrophosphate group. In certain aspects, cleavage of the pyrophosphate switches the fluorophore moiety into a fluorescent state i.e., the fluorophore is dequenched. This event can then be detected using an ultrasensitive fluorescence detector. Using single molecule detection for example, fluorescent signals appear at the locations of the individual molecules being observed. In certain aspects, each type of nucleotide is labeled with a different fluorophore so that the incorporated nucleobases can be sequentially identified by the released fluorophores. Preferably, the nucleotide triphosphate (NTP) of the present methods include, but are not limited to, deoxyadenosine triphosphate, deoxycytosine triphosphate, deoxyguanosine triphosphate, deoxythymidine triphosphate, deoxyuridine triphosphate or mixtures thereof, each with a unique fluorophore attached to the γ-phosphate.

As is described in detail hereinbelow, the nucleotides of the present invention, both purine and pyrimidine varieties, are modified at various sites with a fluorophore moiety and a quencher moiety. In certain aspects, the combination of fluorophore and quencher are attached to the same position of the nucleotide separated by a linker. In others aspects, the moieties are at distinct points on the nucleotide. Once the quenched dNTPs are produced, they can be used to sequence DNA strands by direct single molecule detection. The fluorescence is detected when the labeled dNTPs are incorporated into the strand (the de-quenching event), and fluorescence is induced. The ultrasensitivity of the present methods provide unprecedented economy and represent substantial improvements over the methods of the prior art.

Single molecule detection using methods of the present invention is illustrated in FIG. 2. In certain embodiments, an unlabeled, single-stranded target nucleic acid with a primer hybridized thereto is tethered to the surface of a solid support such as a glass slide. An aqueous solution comprising an enzyme, such as a DNA polymerase, and fluorogenic dNTPs flows across the surface. Alternatively, in another embodiment, an individual polymerase molecule is immobilized on a glass slide and the polymerase is bathed in a flowing solution comprising: 1) unlabeled, single-stranded DNA fragments hybridized to an oligonucleotide primer and 2) a mixture of deoxynucleotide triphosphates, each uniquely labeled with a different color of fluorescent dye attached to the γ-phosphate.

An evanescent light field is set up by total internal refection (TIR) of a laser beam at the glass-aqueous solution interface. In certain aspects, the TIR illumination field is continuously imaged at video-rate with an intensified charge couple device (ICCD) camera.

With reference to FIG. 2B, non-fluorescent dNTPs (small circles) cannot be detected until incorporated into DNA (lines) by a polymerase (large circle). Upon incorporation, a fluorescent dye molecule (spiked circle) is released with pyrophosphate from the polymerase. The released dye is thereafter swept away from the parent DNA molecule by the flow (see, FIG. 2C). The CCD camera records the progress of the polymerase as it moves along the DNA, releasing dyes sequentially.

B. Solid Phase

The present invention relates to a heterogenous assay wherein a material in the solid-phase interacts with reagents in the liquid phase. In certain aspects, the nucleic acid is attached to the solid phase. The nucleic acid can be in the solid phase such as immobilized on a solid support, through any one of a variety of well-known covalent linkages or non-covalent interactions. The support is comprised of insoluble materials, such as controlled pore glass, a glass plate or slide, polystyrene, acrylamide gel and activated dextran. In other aspects, the support has a rigid or semi-rigid character, and can be any shape, e.g. spherical, as in beads, rectangular, irregular particles, gels, microspheres; or substantially flat, so long as the support permits single molecule detection. In some embodiments, it can be desirable to create an array of physically separate sequencing regions on the support with, for example, wells, raised regions, dimples, pins, trenches, rods, pins, inner or outer walls of cylinders, and the like. Other suitable support materials include, but are not limited to, agarose, polyacrylamide, polystyrene, polyacrylate, hydroxethylmethacrylate, polyamide, polyethylene, polyethyleneoxy, or copolymers and grafts of such. Other embodiments of solid-supports include small particles, non-porous surfaces, addressable arrays, vectors, plasmids, or polynucleotide-immobilizing media.

As used in the methods of the present invention, nucleic acid can be attached to the solid support by covalent bonds, or other affinity interactions, to chemically reactive functionality on the solid-supports. The nucleic acid can be attached to solid-supports at their 3', 5', sugar, or nucleobase sites. In certain embodiments, the 3' site for attachment via a linker to the support is preferred due to the many options available for stable or selectively cleavable linkers. Immobilization is preferably accomplished by a covalent linkage between the support and the nucleic acid. The linkage unit, or linker, is designed to be stable and facilitate accessibility of the immobilized nucleic acid to its sequence complement. Alternatively, non-covalent linkages such as between biotin and avidin or stepavidin are useful. Examples of other functional group linkers include ester, amide, carbamate, urea, sulfonate, ether, and thioester. A 5' or 3' biotinylated nucleotide can be immobilized on avidin or strepavidin bound to a support such as glass.

In other aspects of the heterogenous assay of the present invention, the polymerase is immobilized on a solid support. Suitable solid supports include, but are not limited to, controlled pore glass, a glass plate or slide, polystyrene, and activated dextran. In other aspects, synthetic organic polymers such as polyacrylamide, polymethacrylate, and polystyrene are also illustrative support surfaces. In addition, polysaccharides such as cellulose and dextran, are further illustrative examples of support surfaces. Other support surfaces such as fibers are also operable.

In other aspects, polymerase immobilization is accomplished using solid chromatography resins, that have been modified or activated to include functional groups that permit the covalent coupling of resin to enzyme. Typically, aliphatic linker arms are employed. The enzymes of the present invention can also be noncovalently attached to a solid support surface, through, for example, ionic or hydrophobic mechanisms.

In a preferred embodiment, covalent attachment of a protein or nucleic acid to a glass or metal oxide surface can be accomplished by first activating the surface with an amino silane. DNA or protein derivatized with amine-reactive functional groups can then attach to the surface (see, K. Narasimhan et al., *Enzyme Microb. Technol.* 7, 283 (1985); M. J. Heller et al., U.S. Pat. No. 5,605,662; and A. N. Asanov et al., *Anal. Chem.* 70, 1156 (1998)).

The ordinarily skilled artisan will know numerous other schemes for linking nucleic acid and proteins to support surfaces. Moreover, the choice of support surface and the method of immobilizing the enzyme is largely a matter of convenience and depends on the practitioner's familiarity with, and preference for, various supports surfaces, as well as preference for various immobilizing schemes, and knowledge of the substrate.

In assay operation, the enzyme, such as a DNA polymerase, selects a single DNA molecule from solution. The polymerase incorporates a first nucleotide at the 3'-end of the primer strand. The polymerase then translocates to the next position on the target DNA, incorporates a complementary nucleotide, and releases the respective pyrophophate-dye. The released dyes move away from the immobilized enzyme in the flowing sample solution. These events can then be recorded sequentially by video-rate imaging using for example, a CCD camera, capable of detecting single fluorophore molecules. The resulting movie shows the activity of a single polymerase molecule operating on a single molecule of DNA. The nucleotide sequence of the DNA target is read directly from the order of released dyes. When the first nucleic acid molecule has been sequenced, the polymerase releases it and selects another template from solution. Many DNA molecules are thereby sequenced by a single polymerase. The process continues for the life of the enzyme.

C. Preparation of Target Nucleic Acid

The target nucleic acid can be prepared by various conventional methods. For example, target nucleic acid can be prepared as inserts of any of the conventional cloning vectors, including those used in conventional DNA sequencing. Extensive guidance for selecting and using appropriate cloning vectors is found in Sambrook et al., *Molecular Cloning: A Laboratory Manual,* Second Edition (Cold Spring Harbor Laboratory, New York, 1989), and like references. Sambrook et al. and Innis et al, editors, PCR Protocols (Academic Press, New York, 1990) also provide guidance for using polymerase chain reactions to prepare target polynucleotides. Cloned or PCR-amplified target nucleic acid is prepared which permit attachment to solid supports.

In a preferred embodiment, sheared DNA fragments from a subject organism, preferably human, are treated to provide blunt ends, then ligated to two oligodeoxynucleotides (ODNs). The first ODN is derivatized with biotin and the second is complementary to a sequencing primer. The ligated DNA is denatured, it is brought into contact with a streptavidin-activated slide, and it attaches through the biotin to the slide. A primer is hybridized to the tethered fragments prior to sequencing. Only DNA fragments having each type of ODN can both attach and be sequenced; fragments having two primer ODNs will not attach, and those having two attachment ODNs will not prime. DNA attachment could also be accomplished by direct covalent coupling as practiced on DNA chips (see, U.S. Pat. No. 5,605,662). Unlike DNA chips that require a dense lawn of probes, preferably, a few DNA molecules are bound per unit surface area. Binding density is easily controlled by adding a carrier to the DNA sample (e.g. free biotin to a biotinylated DNA sample).

D. Detection

In certain embodiments, the enzymatic reaction is monitored using single molecule detection. The single-molecule fluorescence detection of the present invention can be practiced using optical setups including near-field scanning microscopy, far-field confocal microscopy, wide-field epi-illumination, and total internal reflection fluorescence (TIRF) microscopy. Suitable photon detectors include, but are not limited to, photodiodes and intensified CCD cameras. In a preferred embodiment, an intensified charge couple device (ICCD) camera is used. The use of a ICCD camera to image individual fluorescent dye molecules in a fluid near the surface of the glass slide is advantageous for several reasons. With an ICCD optical setup, it is possible to acquire a sequence of images (movies) of fluorophores. In certain aspects, each of the NTPs of the present invention has a unique fluorophore associated with it, as such, a four-color instrument can be used having four cameras and four exitation lasers. Thus, it is possible to use this optical setup to sequence DNA. In addition, many different DNA molecules spread on a microscope slide can be imaged and sequenced simultaneously. Moreover, with the use of image analysis algorithms, it is possible to track the path of single dyes and distinguish them from fixed background fluorescence and from "accidentally dequenched" dyes moving into the field of view from an origin upstream.

In certain aspects, the preferred geometry for ICCD detection of single-molecules is total internal reflectance fluorescence (TIRF) microscopy. In TIRF, a laser beam totally reflects at a glass-water interface. The field does not end abruptly at the reflective interface, but its intensity falls off exponentially with distance. The thin "evanescent" optical field at the interface provides low background and enables the detection of single molecules with signal-to-noise ratios of 12:1 at visible wavelengths (see, M. Tokunaga et al., *Biochem. and Biophys. Res. Comm.* 235, 47 (1997) and P. Ambrose, *Cytometry,* 36, 244 (1999)).

The penetration of the field beyond the glass depends on the wavelength and the laser beam angle of incidence. Deeper penetrance is obtained for longer wavelengths and for smaller angles to the surface normal within the limit of a critical angle. In typical assays, fluorophores are detected within about 200 nm from the surface which corresponds to the contour length of about 600 base pairs of DNA. Preferably, a prism-type TIRF geometry for single-molecule imaging as described by Xu and Yeung is used (see, X-H.N. Xu et al., *Science,* 281, 1650 (1998)).

DNA, proteins and lipids have all been detected in complex samples with single-molecule sensitivity using labeled probes (see, L. Edman et al., *Proc. Natl. Acad. Sci. USA,* 93, 6710 (1996); M. Kinjo et aL, *Nucleic Acids Res.* 23, 1795 (1995); A. Castro and J. G. K. Williams, *Anal. Chem.* 69, 3915 (1997); S. Nie, et al., *Science* 266, 1018 (1994); S. Nie, et al., *Anal. Chem.* 67, 2849 (1995); and T. Schmidt et al., *Proc. Natl. Acad. Sci. USA* 9, 2926 (1996)). In addition to simple detection, single fluorophores are also characterized with respect to fluorescence lifetime, spectral shifts and rotational orientation. In a preferred aspect of the present invention, an aqueous solution comprising an enzyme, such as a DNA polymerase, and distinguishable fluorogenic dNTPs, i.e., a characteristic dye for each nucleobase, flows across the surface. An evanescent light field is set up by total internal refection (TIR) of a laser beam at the glass-aqueous solution interface. In certain aspects, the TIR illumination field is continuously imaged at video-rate with an intensified charge couple device (ICCD) camera. It is thus possible to image the pyrophosphate as it is hydrolyzed by the enzyme.

Upon incorporation by polymerase, the dNTP is hydrolyzed as usual and the liberated pyrophosphate-dye moiety diffuses into the surrounding medium. The free dye molecule, now unquenched, becomes fluorescent and its appearance is imaged at video-rate under a microscope. A flowing stream sweeps the dye away from the parent DNA molecule. As the polymerase continues to move along the DNA, the nucleotide sequence is read from the order of released dyes. Sequencing proceeds quickly, as fast as the polymerase progresses along the DNA template.

In another embodiment, the present invention includes sensors as disclosed in U.S. Pat. No. 5,814,524 which issued to Walt et al., on Sep. 29, 1998. An optical detection and identification system is disclosed therein that includes an optic sensor, an optic sensing apparatus and methodology for detecting and evaluating one or more analytes or ligands of interest, either alone or in mixtures. The system is comprised of a supporting member and an array formed of heterogeneous, semi-selective polymer films which function as sensing receptor units and are able to detect a variety of different analytes and ligands using spectral recognition patterns. Using this system, it is possible to combine viewing and chemical sensing with imaging fiber chemical sensors.

E. High Throughput Screening

The present invention also provides integrated systems for high-throughput screening of DNA sequencing and pyrophosphate detection. The systems typically include robotic armature which transfers fluid from a source to a destination, a controller which controls the robotic armature, an ICCD camera, a data storage unit which records the detection, and an assay component such as a microtiter dish or a substrate comprising a fixed reactant. A number of robotic fluid transfer systems are available, or can easily be made from existing components. For example, a Zymate XP (Zymark Corporation; Hopkinton, Mass.) automated robot using a Microlab 2200 (Hamilton; Reno, Nev.) pipetting station can be used to transfer parallel samples to 96 well microtiter plates to set up several parallel simultaneous polymerase reactions.

Optical images viewed (and, optionally, recorded) by a camera or other recording device (e.g., a photodiode and data storage device) are optionally further processed in any of the embodiments herein, e.g., by digitizing the image and storing and analyzing the image on a computer. A variety of commercially available peripheral equipment and software is available for digitizing, storing and analyzing a digitized video or digitized optical image. In certain aspects, the integrated system of the present invention carries light from the specimen field to the charge-coupled device (CCD) camera, which includes an array of picture elements (pixels). The light from the specimen is imaged on the CCD camera. Particular pixels corresponding to regions of the specimen (e.g., individual polymerase sites on a glass surface) are sampled to obtain light intensity readings for each position. Multiple pixels are processed in parallel to increase speed. The apparatus and methods of the invention are easily used for viewing any sample, e.g., by fluorescent or dark field microscopic techniques.

II. Compounds

A. Attachment of a γ-Phosphate Fluorophore

In certain aspects, the methods of the present invention comprise detecting and identifying individual fluorogenic dNTP molecules as a polymerase incorporates them into a single DNA molecule. In certain aspects, a fluorescent dye is attached to the γ-phosphate and a quencher is attached to the nucleobase. As such, the present invention provides a nucleotide triphosphate (NTP) probe, comprising: a NTP having a γ-phosphate with a fluorophore moiety attached thereto; a quencher moiety sufficiently proximal to the fluorophore moiety to prevent fluorescence of the fluorophore moiety; wherein the fluorophore moiety exists quenched with at least about a 5 fold quenching efficiency, preferably, at least a 10 fold quenching efficiency, when the γ-phosphate is attached to the NTP and unquenched when the γ-phosphate is detached from the NTP. In preferred aspect, the NTP probe is a dNTP probe having a fluorescent dye attached to the γ-phosphate moiety and a quencher attached to the nucleobase. Suitable nucleobases include, but are not limited to, adenine, guanine, cytosine, uracil, thymine, deazaadenine and deazaguanosine. The quenched dNTPs are non-fluorescent when the γ-phosphate is attached to the NTP, and thereafter become fluorescent when the γ-phosphate is unattached to the NTP.

B. Fluorescence Quenching

In single molecule detection, high quenching efficiency is advantageous as it reduce fluorescence background, thus permitting the use of higher nucleotide concentrations. Several quenching mechanisms exist (see, for example, G. G. Guilbault, *Practical Fluorescence*, Marcel Dekker, New York, 1973). In certain instances, the quenching depends on spectral overlap between fluorophore and quencher, and it functions at long range (fluorescence resonance energy transfer, FRET). In other instances, the fluorophore and quencher interact between molecular orbitals and require contact between fluorophore and quencher e.g. electron transfer mechanisms. In still other instances, a ground-state complex quenching mechanism can occur. All such quenching mechanisms are within the scope of the present invention.

In certain aspects, the fluorophore moiety are fluorescent organic dyes derivatized for attachment to γ-phosphate directly or via a linker. Preferably, quencher moieties are also organic dyes, which may or may not be fluorescent, depending on the particular embodiment of the invention. For example, in one embodiment of the present invention, the fluorophore and the quencher are both fluorescent. In this embodiment, a fluorescent energy transfer mechanism can be used wherein the first fluorophore (e.g. fluorescein) is excited and emission is read from the second fluorophore (e.g. rhodamine). In these systems, dequenching is accomplished by hydrolysis of the fluorophore attached to the γ-phosphate.

Figure 3:
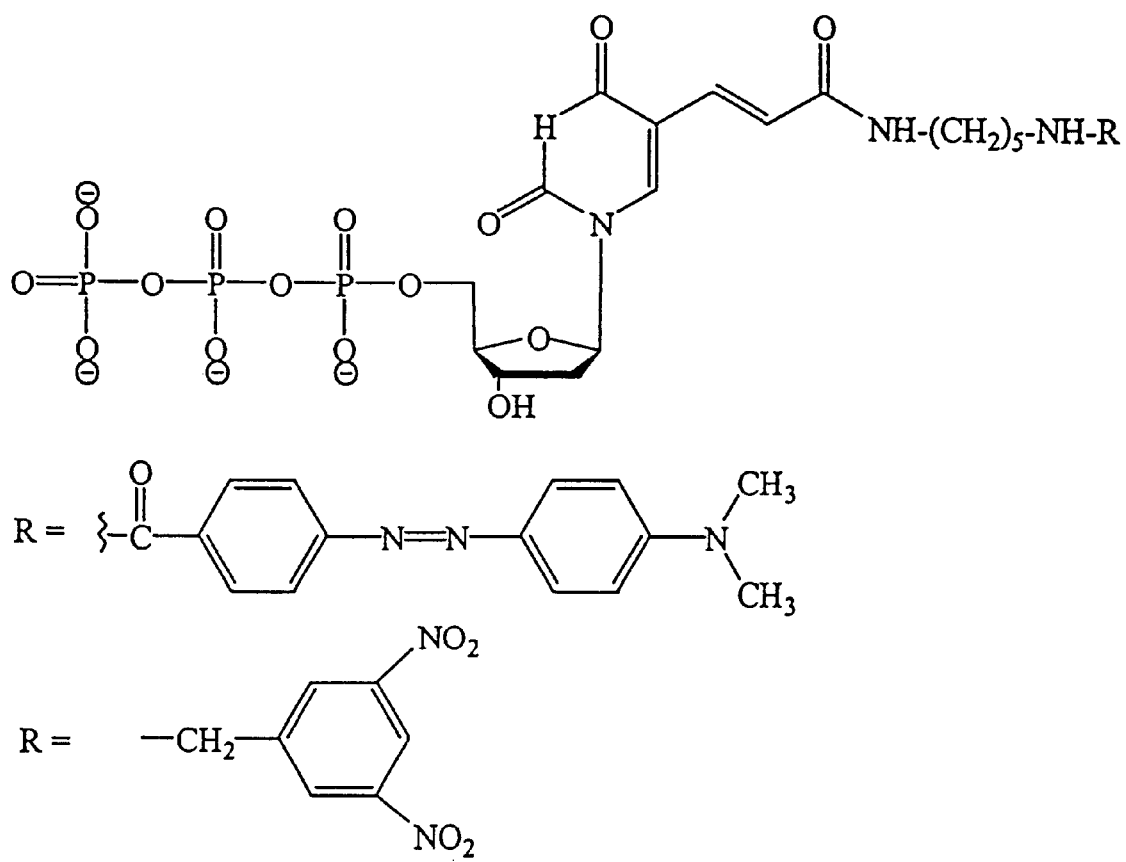
FIG. 3 illustrates DABCYL and dinitrophenyl derivatives of the present invention.

In another embodiment, the fluorophore and quencher function by an electron transfer mechanism. In this aspect, a non-fluorescent quencher e.g. DABCYL or dinitrophenyl (see, FIG. 3) absorbs energy from an excited fluorophore, but does not release the energy radiatively. These quenchers can be referred to as chromogenic molecules.

There is a great deal of practical guidance available in the literature for providing an exhaustive list of fluorescent and chromogenic molecules and their relevant optical properties (see, for example, Berlman, *Handbook of Fluorescence Spectra of Aromatic Molecules*, 2nd Edition (Academic Press, New York, 1971); Griffiths, *Colour and Constitution of Organic Molecules* (Academic Press, New York, 1976); Bishop, Ed., Indicators (Pergamon Press, Oxford, 1972); Haugland, *Handbook of Fluorescent Probes and Research Chemicals* (Molecular Probes, Eugene, 1992) Pringsheim, *Fluorescence and Phosphorescence* (Interscience Publishers, New York, 1949); and the like. Further, there is extensive guidance in the literature for derivatizing fluorophore and quencher molecules for covalent attachment via common reactive groups that can be added to a nucleotide, as exemplified by the following references: Haugland (supra); Ullman et al., U.S. Pat. No. 3,996,345; Khanna et al., U.S. Pat. No. 4,351,760.

Suitable donors and acceptors operating on the principle of fluorescence energy transfer (FRET) include, but are not limited to, 4-acetamido-4'-isothiocyanatostilbene-2, 2'disulfonic acid; acridine and derivatives: acridine, acridine isothiocyanate; 5-(2'-amninoethyl)aminonaphthalene-1-sulfonic acid (EDANS); 4-amino-N-[3-vinylsulfonyl) phenyl]naphthalimide-3,5disulfonate; N-(4-anilino-1-naphthyl)maleimide; anthranilamide; BODIPY; Brilliant Yellow; coumarin and derivatives: coumarin, 7-amino-4-methylcoumarin (AMC, Coumarin 120),7-amino-4-trifluoromethylcouluarin (Coumaran 151); cyanine dyes; cyanosine; 4',6-diarninidino-2-phenylindole (DAPI); 5', 5"-dibromopyrogallol-sulfonaphthalein (Bromopyrogallol Red); 7-diethylamino-3-(4'-isothiocyanatophenyl)-4-methylcoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino]naphthalene-1-sulfonyl chloride (DNS, dansylchloride); 4-dimethylaminophenylazophenyl-4'-isothiocyanate (DABITC); eosin and derivatives: eosin, eosin isothiocyanate, erythrosin and derivatives: erythrosin B, erythrosin, isothiocyanate; ethidium; fluorescein and derivatives: 5-carboxyfluorescein (FAM),5-(4,6-dichlorotriazin-2-yl)aminofluorescein (DTAF),2',7'- dimethoxy-4'5'-dichloro-6-carboxyfluorescein (JOE), fluorescein, fluorescein isothiocyanate, QFITC, (XRITC); fluorescamine; IR144; IR1446; Malachite Green isothiocyanate; 4-methylumbelliferoneortho cresolphthalein; nitrotyrosine; pararosaniline; Phenol Red; B-phycoerythrin; o-phthaldialdehyde; pyrene and derivatives: pyrene, pyrene butyrate, succinimidyl 1-pyrene; butyrate quantum dots; Reactive Red 4 (Cibacron™ Brilliant Red 3B-A) rhodamine and derivatives: 6-carboxy-X-rhodamine (ROX), 6-carboxyrhodamine (R6G), lissamine rhodamine B sulfonyl chloride rhodamine (Rhod), rhodamine B, rhodamine 123, rhodamine X isothiocyanate, sulforhodamine B, sulforhodamine 101, sulfonyl chloride derivative of sulforhodamine 101 (Texas Red); N,N,N',N'-tetramethyl-6-carboxyrhodamine (TAMRA); tetramethyl rhodamine; tetramethyl rhodamine isothiocyanate (TRITC); riboflavin; rosolic acid; terbium chelate derivatives; Cy 3; Cy 5; Cy 5.5; Cy 7; IRD 700; IRD 800; La Jolla Blue; phthalo cyanine; and naphthalo cyanine.

Preferred fluorophore-quencher pairs include, but are not limited to, xanthene dyes, including fluoresceins, and rhodamine dyes. Many suitable forms of these compounds are widely available commercially with substituents on their phenyl moieties which can be used as the site for bonding or as the bonding functionality for attachment to the γ-phosphate or nucleobase. Another group of fluorescent compounds are the naphthylamines, having an amino group in the alpha or beta position. Included among such naphthylamino compounds are 1-dimethylaminonaphthyl-5-sulfonate, 1 -anilino-8-naphthalene sulfonate and 2-p-toluidinyl-6-naphthalene sulfonate. Other dyes include 3-phenyl-7-isocyanatocoumarin, acridines, such as 9-isothiocyanatoacridine and acridine orange; N-(p-(2-benzoxazolyl)phenyl)maleimide; benzoxadiazoles, stilbenes, pyrenes, and the like.

Preferably, the fluorophore/quencher pair are selected from fluorescein and rhodamine dyes. These dyes and appropriate linking methodologies for attachment to nucleotides are described in many references. (see, Khanna et al. (cited above); Marshall, *Histochemical J.*, 7:299–303 (1975); Menchen et al., U.S. Pat. No. 5,188,934; Menchen et al., European Patent Application 87310256.0; and U.S. Pat. No. 5,366,860, issued to Bergot et al.).

In a preferred embodiment, the quencher 4-(4'-dimethylaminophenylazo)-benzoic acid (DABCYL) is used. The quencher DABCYL (see, FIG. 3) is commonly used in fluorogenic probes to detect DNA hybridization (molecular beacons) or protease activity. DABCYL quenches fluorescence from a wide variety of dyes emitting between 475 nm and 805 nm, with measured efficiencies ranging from 90 to 99.9% (see, S. Tyagi et al., *Nat. Biotechnol.* 16, 49 (1998); and G.T. Wang et al., *Tetrahedron Lett.* 31, 6493 (1990)). Without being bound by any particular theory, it is believed that the quenching mechanism of DABCYL probably involves electron transfer, rather than fluorescence resonance energy transfer, because it is wavelength-independent. In an equally preferred embodiment, the quenchers dinitrophenyl (DNP) or trinitrophenyl (TNP) are used.

Quenching efficiency as measured in any particular experiment depends on the purity of the dye-quencher pair (contaminating free dye or cleaved molecules fluoresce); the electronic coupling and physical distance between dye and quencher (closer is usually better); and the excited-state lifetime of the dye (the longer the time, the greater the chances for electron transfer).

In certain embodiments, certain visible and near IR dyes are known to be sufficiently fluorescent and photostable to be detected as single molecules. In this aspect the visible dye, BODIPY R6G (525/545), and a larger dye, LI-COR's near-infrared dye, IRD-38 (780/810) can be detected with single-molecule sensitivity and are used to practice the present invention.

There are many linking moieties and methodologies for attaching fluorophore or quencher moieties to nucleotides, as exemplified by the following references: Eckstein, editor, *Oligonucleotides and Analogues: A Practical Approach* (IRL Press, Oxford, 1991); Zuckerman et al., *Nucleic Acids Research*, 15: 5305–5321 (1987) (3' thiol group on oligonucleotide); Sharma et al., *Nucleic Acids Research*, 19: 3019 (1991) (3' sulfhydryl); Giusti et al., PCR *Methods and Applications*, 2: 223–227 (1993) and Fung et al., U.S. Pat. No. 4,757,141 (5' phosphoamino group via Aminolink™ II available from Applied Biosystems, Foster City, Calif.) Stabinsky, U.S. Pat. No. 4,739,044 (3' aminoalkylphosphoryl group); AP3 Labeling Technology (U.S. Pat. Nos. 5,047, 519 and 5,151,507, assigned to E.I. DuPont de Nemours & Co); Agrawal et al., *Tetrahedron Letters*, 31: 1543–1546 (1990) (attachment via phosphoramidate linkages); Sproat et al., *Nucleic Acids Research*, 15: 4837 (1987) (5' mercapto group); Nelson et al., *Nucleic Acids Research*, 17: 7187–7194 (1989) (3' amino group); and the like.

Figure 4:
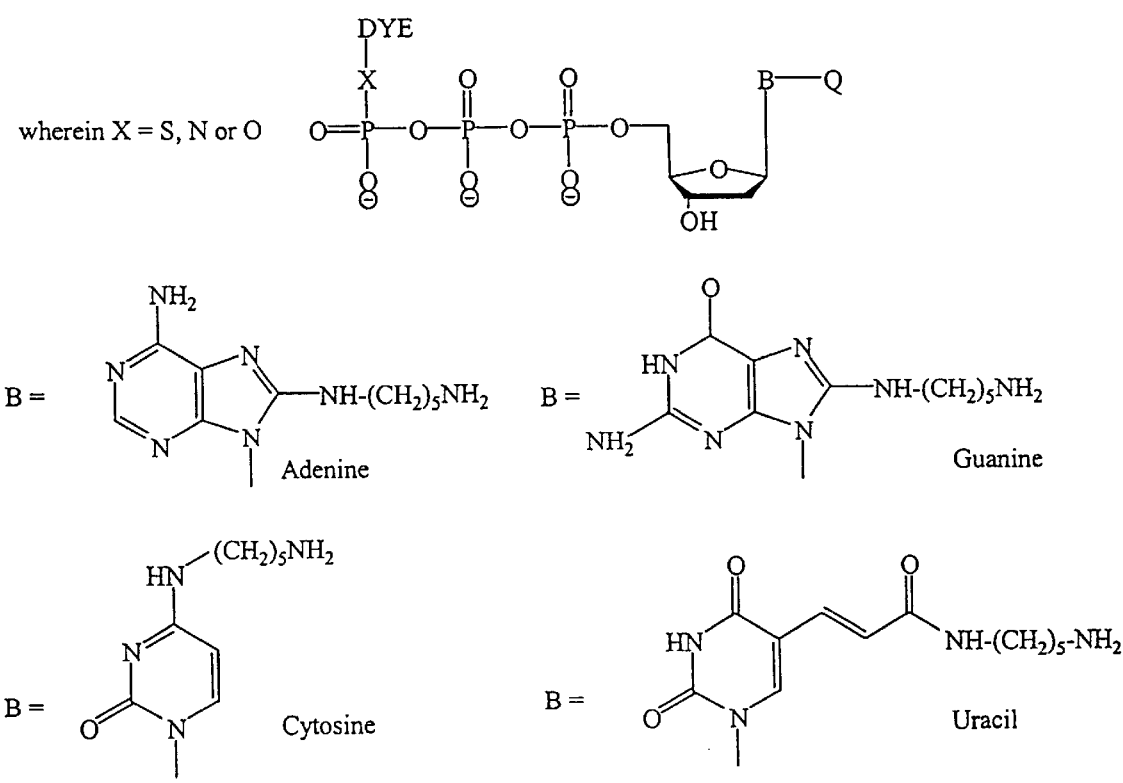
FIG. 4 illustrates compounds of the present invention.

With reference to FIG. 4, the preferred linkers to several bases of various dNTP structures of the present invention are shown. Again, DABCYL is a wavelength-independent fluorescence quencher having quenching efficiencies in the range required by the present methods. Better quenching permits higher dNTP concentrations and faster turnover rates. In certain aspects, the quencher is linked to the same nucleobase sites typically employed for attaching dyes (see, FIG. 3). As the polymerase progresses along the DNA, the quencher will remain at every incorporated base. In certain aspects, the quencher is covalently attached to a dNTPs using the C5 linker shown in FIG. 3. In certain embodiments, the quencher moiety is attached to the fluorophore moiety via a linker. In certain other embodiments, the quencher can be attached to the sugar of the dNTPs.

In general, nucleotide labeling can be accomplished using any of a large number of known nucleotide labeling techniques using known linkages, linking groups, and associated complementary functionalities. The linkage linking the quencher moiety and nucleotide should be compatible with relevant polymerases and not quench the fluorescence of the fluorophore moiety.

Preferably, the quenchers are covalently linked to the 5-carbon of pyrimidine bases and to the 7-carbon of 7-deazapurine bases. Several suitable base labeling procedures have been reported that can be used with the present invention, e.g. Gibson et al., *Nucleic Acids Research*, 15: 6455–6467 (1987); Gebeyehu et al., *Nucleic Acids Research*, 15: 4513–4535 (1987); Haralarnbidis et al., *Nucleic Acids Research*, 15: 4856–4876 (1987); Nelson et al., *Nucleosides and Nucleotides*, 5(3) 233–241 (1986); Bergstrom, et al., *JACS*, 111, 374–375 (1989); U.S. Pat. Nos. 4,855,225, 5,231,191, and 5,449,767, each of which is incorporated herein by reference. Preferably, the linkages are acetylenic amido or alkenic amido linkages, the linkage between the quencher and the nucleotide base being formed by reacting an activated N-hydroxysuccinimide (NHS) ester of the dye with an alkynylamino- or alkenylamino-derivatized base of a nucleotide. More preferably, the resulting linkages are shown in FIG. 4.

The synthesis of alkynylamino-derivatized nucleosides is taught by Hobbs et al. in European Patent Application No. 87305844.0; U.S. Pat. Nos. 5,047,519 and 5,151,507, assigned to E.I. DuPont de Nemours & Co; and Hobbs et al., *J. Org. Chem.*, 54: 3420 (1989), which are incorporated herein by reference. As taught therein, the alkynylamino-derivatized nucleotides are formed by placing the appropriate halodeoxynucleoside (usually 5-iodopyrimidine and 7-iodo-7-deazapurine deoxynucleosides and Cu(I) in a flask, flushing, with argon to remove air, adding dry DMF, followed by addition of an alkynylamine, triethyl-amine and Pd(0). The reaction mixture can be stirred for several hours, or until thin layer chromatography indicates consumption of the halodeoxynucleoside.

As taught in U.S. Pat. No. 5,047,519, which issued to Hobbs et al. on Sep. 10, 1991, the alkynylamino linkers have the structure:

Nuc—C≡C—R$^1$—NR$^2$R$^3$ wherein R$^1$ is a substituted or unsubstituted diradical moiety of 1–20 atoms. Nuc is a purine or pyrimidine base. R$^1$ can be straight-chained alkylene, C$_1$–C$_{20}$, optionally containing, within the chain double bonds, triple bonds, aryl groups or heteroatoms such as N, O or S. The heteroatoms can be part of such functional groups as ethers, thioethers, esters, amines or amides. Preferably, R$^1$ is straight-chained alkylene, C$_1$–C$_{20}$; most preferably R$^1$ is CH$_2$. Substituents on R$^1$ can include C$_1$–C$_6$ alkyl, aryl, ester, ether, amine, amide or chloro groups. R$^2$ and R$^3$ are independently H, alkyl, C$_1$–C$_4$, or a protecting group such as acyl, alkoxycarbonyl, a fluorophore, a quencher or sulfonyl. Preferably R$^2$ is H, and R$^3$ is a quencher. The alkynylamino linker is preferably attached to the 5-position of the pyrimidine nucleotides and the 7 position of the purine nucleotides.

Figure 9:
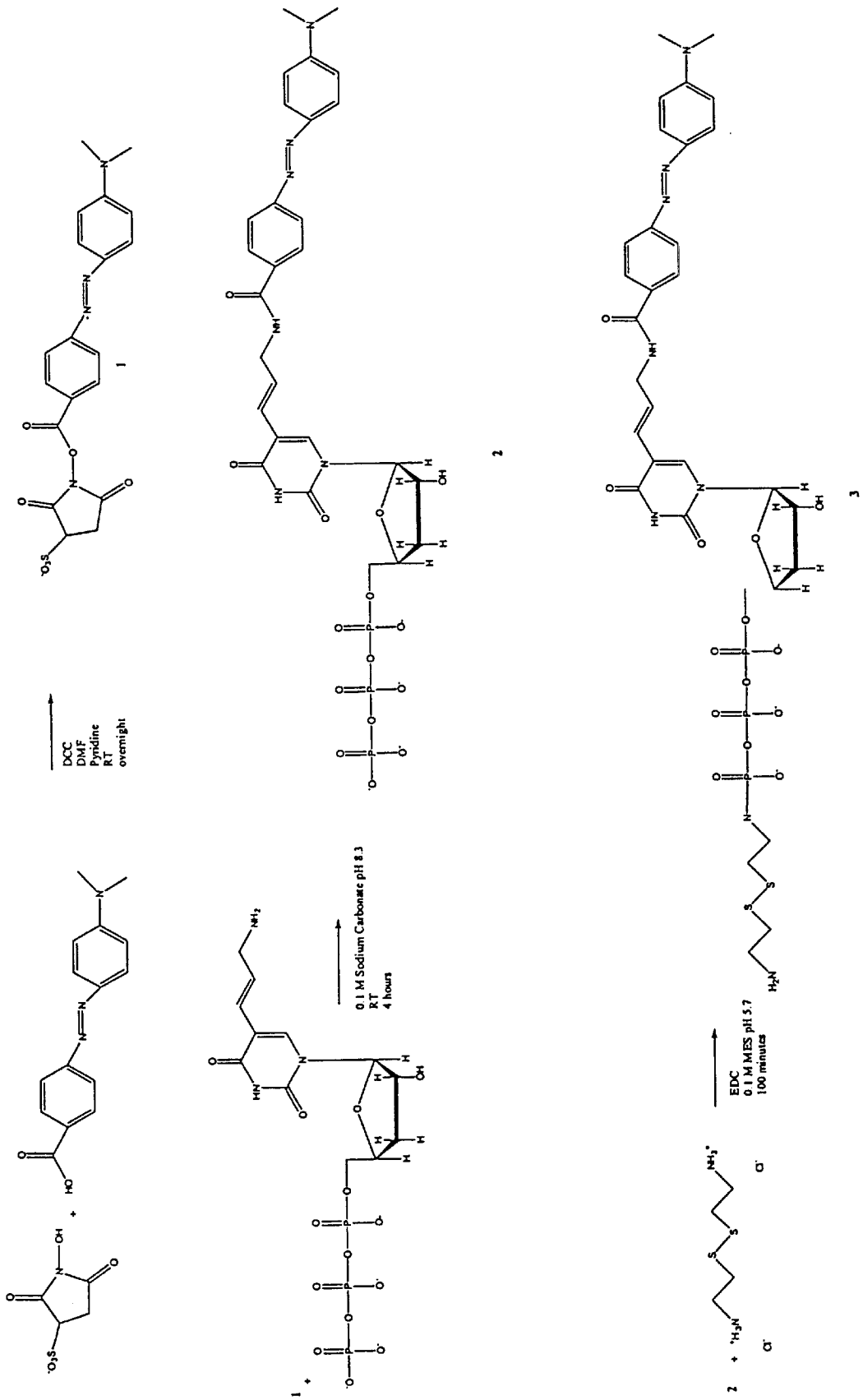
FIG. 9 illustrates synthesis of a compound of the present invention.
Figure 9:
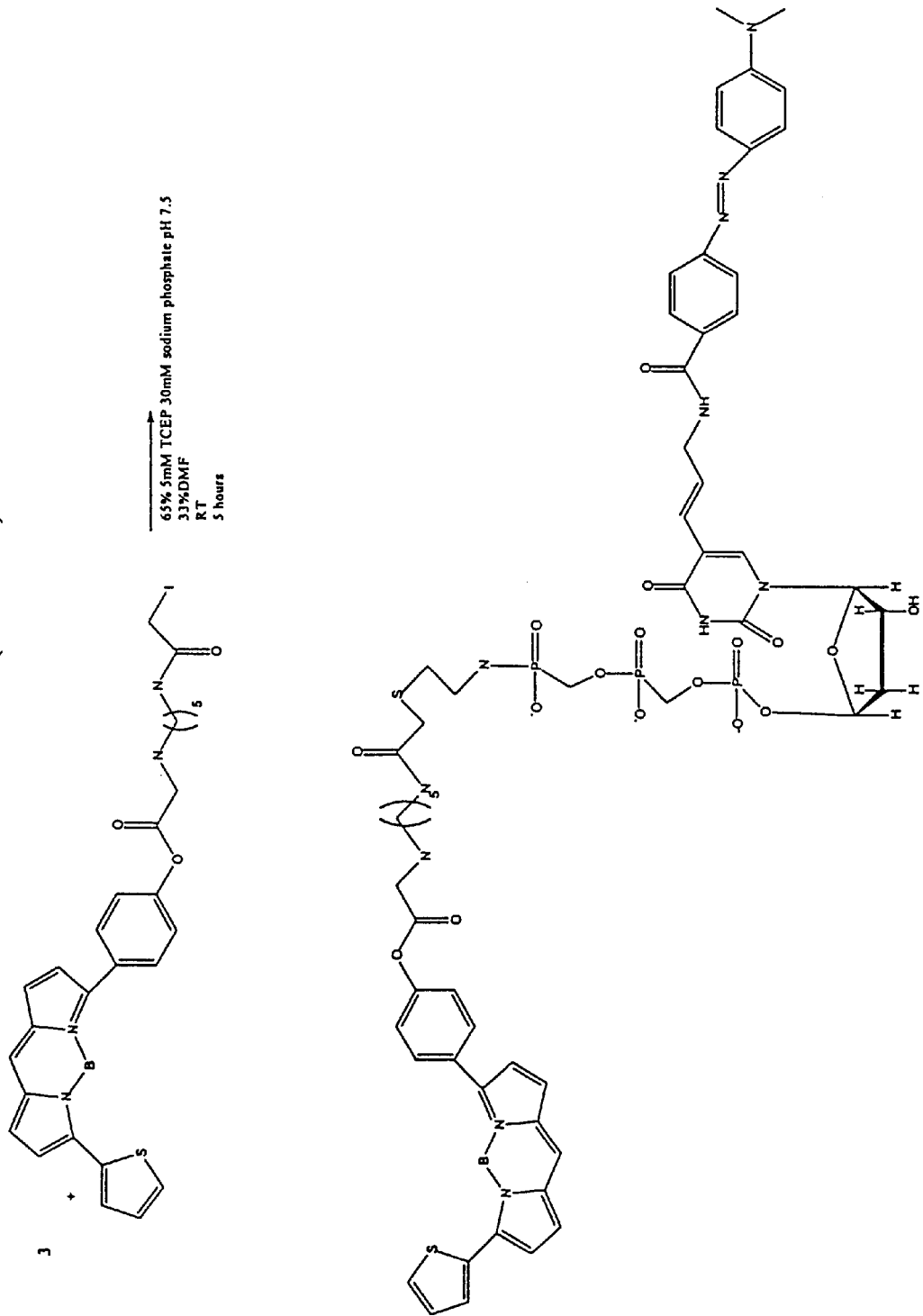

In a preferred embodiment, a quencher-sulfoNHS derivative e.g., DABCYL-sulfoNHS is prepared using DABCYL and reacting it with N-hydroxysulfosuccinimide and N,N'-dicyclohexylcarbodiimide under a nitrogen atmosphere (see, FIG. 9). The DABCYL-sulfoNHS derivative is reacted with an aminoallyl-dNTP e.g. aminoallyl-dUTP, to produce the DABCYL-dUTP. Using the DABCYL-dUTP and cystamine dihydrochloride, a DABCYL-dUTP-thiol derivative can be generated. Thereafter, a NTP having a γ-phosphate fluorophore attached can be produced by reacting for example the DABCYL-dUTP-thiol with BODIPY TR-iodoacetamide (commercially available from Molecular Probes D-6011) to produce DABCYL-dUTP-BODIPY TR.

C. Required Quenching Efficiency

The present invention provides NTP molecules having a γ-phosphate with a fluorophore moiety attached thereto. The fluorophore moiety exists quenched with at least about a 5 fold quenching efficiency when the γ-phosphate is attached to the NTP and is unquenched i.e., is fluorescent, when the γ-phosphate is detached from the NTP. Preferably, the fluorophore moiety exists quenched with at least about a 3 fold quenching efficiency to about 100 fold quenching efficiency. In a more preferred embodiment, the fluorophore moiety exists quenched with at least about a 100 fold quenching efficiency to about a 1000 fold quenching efficiency.

The quenching efficiency of the NTPs of the present invention is a routine parameter easily determined. As will be apparent to those of skill in the art, quenching efficiency can be measured in a fluorometer optionally having laser excitation. Similar to the earlier discussion of the Stem-Volmer equation, quenching efficiency is equal to $$F_o - F/F_o$$

wherein F$_o$ is fluorescence of the NTP without quenching and F is the quenched fluorescence. Since there is no certain way to eliminate all fluorescence in a sample of quenched NTP, the unquenched measurements, F$_o$, can be taken in a separate sample containing dye alone and the quenched measurements, F, can be made on the same concentration of quenched dNTP.

The compounds of the present invention have at least 3 fold quenching efficiency. A fully fluorescent dye has a F$_o$ value of 1, whereas a dye quenched by 90% has an F value of 0.100. A compound quenched by 90%, has a quenching efficiency of 0.9 or is 10 fold quenched. Therefore, for compounds of the present invention, F is characterized as follows: 0.670≦F≦0.999, i.e., the compounds possess quenching efficiencies between about 3 fold to about 1000 fold. Preferably the quenching efficiency of a compound of the present invention is about at least 5 fold to about 1000 fold, and more preferably, the quenching efficiency is about at least 10 fold to about 1000 fold.

In the present invention, detection of pyrophosphate depends on generating a fluorescent signal by dequenching, or turning on, a quenched fluorescent dye in response to pyrophosphate. Efficient quenching provides a lower background fluorescence, enhancing the signal-to-noise ratio upon dequenching by pyrophosphate. Incomplete quenching results in a low level fluorescence background from each dye molecule. Additional background fluorescence is contributed by a few of the dye molecules that are fully fluorescent because of accidental (i.e., pyrophosphate-independent) dequenching, for example by breakage of a bond connecting the dye to the quencher moiety. Thus, the background fluorescence has two components: a low-level fluorescence from all dye molecules, referred to herein as "distributed fluorescence background" and fill-strength fluorescence from a few molecules, referred to herein as "localized fluorescence background".

Without being bound to any particular theory, it is believed that when detecting single molecules, both kinds of background are apparent and their character affects the required amount of quenching needed. In the example wherein a quenched sample imaged by a ICCD camera having an average background fluorescence of 0.1 per pixel, i.e., F is equal to 0.900, and if the background is distributed, with none localized, then each pixel of the ICCD camera will show a fluorescence background of 0.1. The foregoing example assumes a dye concentration that yields one dye molecule per pixel. In this example, a single pyrophosphate-dequenched dye molecule would therefore generate a full-strength signal of 1.0, which is easily distinguished above the uniform low-level background. As the methods and compounds of the present invention minimize localized background, distributed background is the predominate contributor to background fluorescence.

The following examples set forth synthesis methods and methods for using the NTP probes according to the present invention. It is understood that the specific probes, probe constructs and steps of the methods described in these examples are not intended to be limiting. Further objectives and advantages of the present invention other than those set forth above will become apparent from the examples which are not intended to limit the scope of the present invention.

III. EXAMPLES

Example 1

This Example illustrates fluorescence measurement by SMD microscopy and fluorescence quenching and sequencing speed.

A. Fluorescence Measurement by Single-Molecule Detection (SMD) Microscopy

A microscope capable of detecting single fluorescent dye molecules is used to quantitate fluorescence. The laser-illuminated, confocal epifluorescence microscope was constructed after that of Nie et al. (see, Nie, et al., *Anal. Chem.* 67: 2849–2857 (1996)). A pulsed dye laser (1 psec duration, 585 nm) is used for excitation of the fluorophore. The beam is focused into a spot of about 3.4 femtoliter (a cube approximately 1.5 micrometer on edge, or $3.4 \times 10^{-15}$ liter) into a droplet on a coverslip, positioned in the droplet about 25 micrometers from the glass surface to reduce light scattering. Fluorescence is collected with a Nikon oil immersion objective with magnification 100× and N.A.=1.3. The spatial filter has a pinhole of diameter 200 microns, which corresponds to an object space diameter of 2 microns. A custom-made "Raman notch" filter (Kaiser Electro Optics) rejects the 585 nm excitation light with optical density of 7. An interference filter (Omega Optical) passes the fluorescence band and rejects 585 nm with optical density 3.5. The droplet contains a low concentration of dye molecules to minimize the probability of having more than one molecule at a time in the detection volume. Individual dye molecules emit fluorescence photons as they diffuse in and out of the detection volume. A burst of photons is detected when a molecule is present in the detection volume; large burst amplitudes of several dozen photons per millisecond are detected when a molecule passes through the most intense laser light in the center of the beam, while smaller bursts are seen when a molecule passes only through the periphery of the beam. Data is collected for 5–10 minutes. The number of occurrences is tabulated for each observed burst amplitude and a cumulative histogram is constructed (X=burst amplitude; Y=number of bursts>=amplitude X). A threshold is chosen arbitrarily to remove bursts smaller than threshold and results are reported as the number of bursts having an amplitude greater than threshold.

B. dNTP Concentration Affects Reaction Rate According To Michaelis-Menten

In certain embodiments, the methods of the present invention depend on having quenched dNTPs with low fluorescence background. Lower backgrounds allow greater dNTP concentrations and faster sequencing. Conversely, higher backgrounds dictate a lower dNTP concentration, which slows the polymerization rate according to Michaelis-Menten kinetics. With reference to Table 1, 0.06 µM of each dNTP, corresponds to 0.6 molecules per pixel in the illuminated field, and supports a sequencing rate of about 1 base per second. These 0.6 dNTP molecules generate a background fluorescence equivalent to only 0.12 fluorophores per pixel, with 80% quenching. One dNTP fluorophore liberated by a polymerase is easily detected over this low background. Single-molecule error is handled in the same way as commonly practiced in gel-based sequencing, by redundant sequencing of the sample.

TABLE 1

Polymerization Rate vs. dNTP Concentration

| [S], µM ea. dNTP | number of Moles in TIR field | Velocity, nt/sec |
| --- | --- | --- |
| 0.001 | 0.006 | 0.01 |
| 0.003 | 0.029 | 0.05 |
| 0.006 | 0.58 | 0.1 |
| 0.012 | 0.116 | 0.2 |
| 0.03 | 0.288 | 0.5 |
| 0.06 | 0.576 | 1.0 |

TABLE 1-continued

Polymerization Rate vs. dNTP Concentration

| [S], µM ea. dNTP | number of Moles in TIR field | Velocity, nt/sec |
| --- | --- | --- |
| 0.119 | 1.148 | 2.0 |
| 0.295 | 2.842 | 5.0 |
| 0.581 | 5.593 | 10.0 |
| 1.125 | 10.836 | 20.0 |
| 2.571 | 24.768 | 50.0 |

Substrate dNTP concentration affects reaction rate according to Michaelis-Menten kinetics. $v=Vmax^*[S]/(Km+[S])$ Kinetic constants are estimated $Vmax=300s^{-1}$, $K_m=18$ µM based on T7 DNA polymerase, but values vary between publications for the same polymerase and for different polymerases and nucleotides. Molar concentrations are converted to number of molecules in the illuminated detection zone based on its geometry; $(L \times W \times D)=0.2 \times 0.2 \times 0.1)\mu m^3 = 4 \times 10^{-18}$ liters. Total internal reflectance optics are used with a CCD camera.

Example 2

This Example illustrates the synthesis of γ-phosphate modified dNTP's with linkers.

A. DABCYL-dNTP Synthesis

DABCYL-succinimidyl ester (see, FIG. 3, Molecular Probes, Inc.) is conjugated to 5-allylamino dUTP (see, FIG. 4). The synthesized compound is used to screen for polymerases able to incorporate DABCYL at every base.

Figure 5:
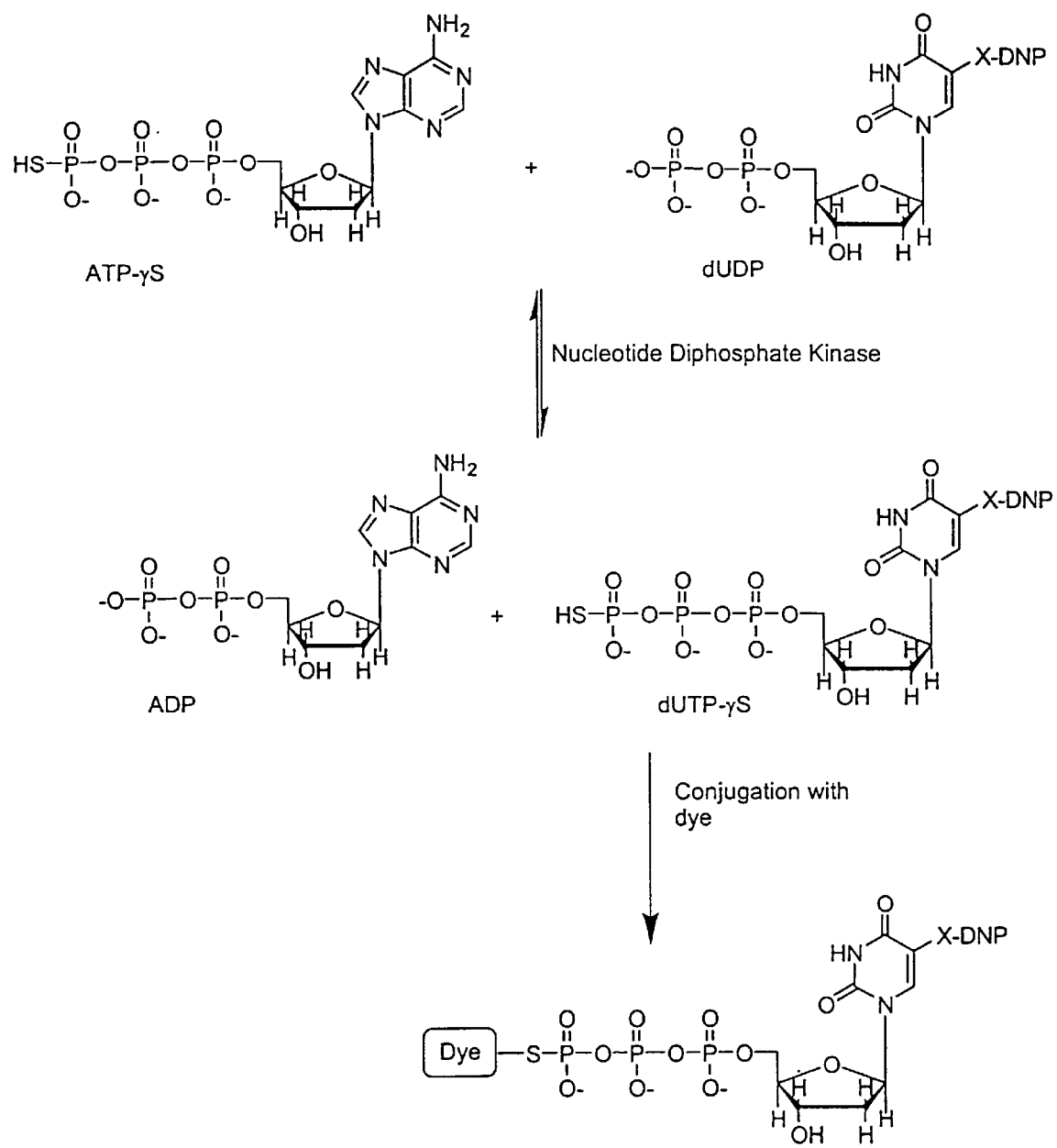
FIG. 5 illustrates synthesis of a compound of the present invention.
Figure 6:
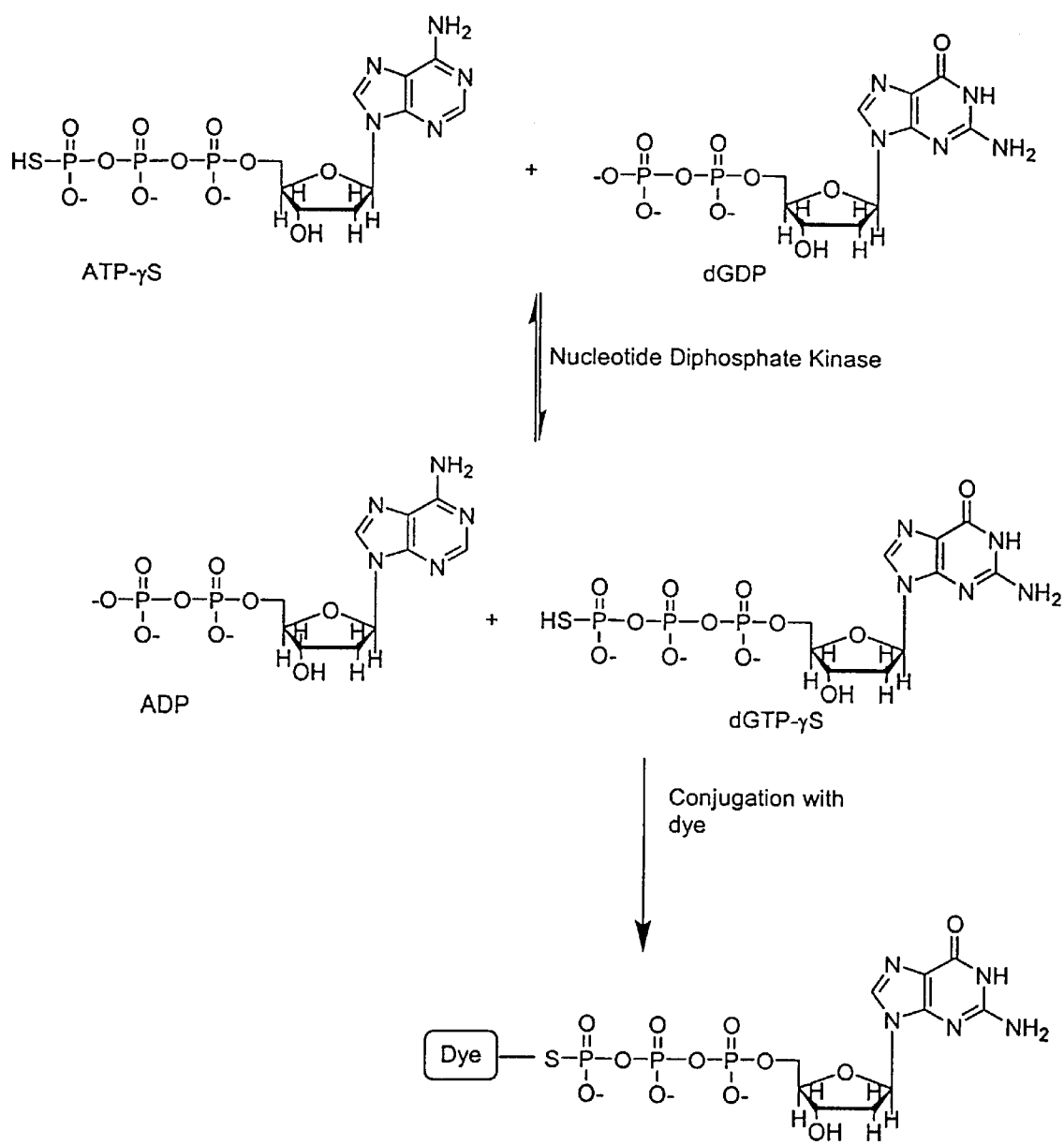
FIG. 6 illustrates synthesis of a compound the present invention.

B. dUTPγS and dATPγS Synthesis dUTPγS is synthesized enzymatically as illustrated in FIG. 5 starting from ATP-γS (Sigma Chemical Company, Milwaukee, Wis.) and using an adaptation of Goody's method (see, R. S. Goody et al., *Biochem. Biophys. Acta.*, 276: 155 (1972)) which is shown in FIG. 6.

C. Thiol-Reactive Dyes Synthesis

Figure 7:
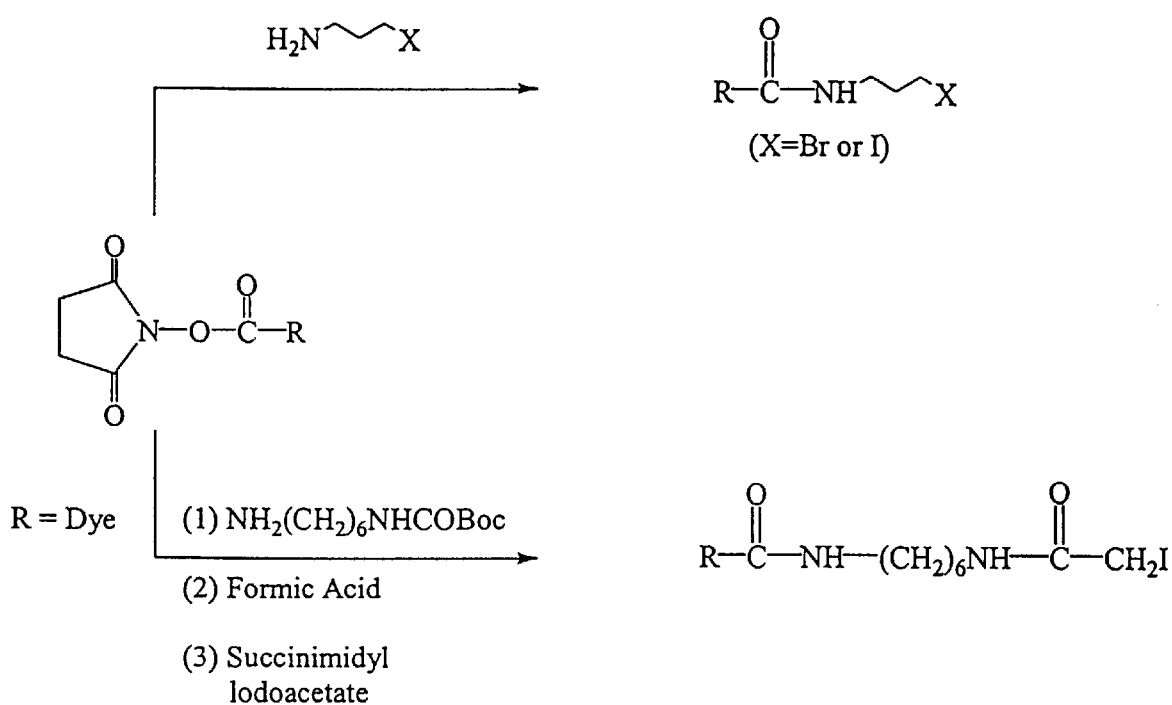
FIG. 7 illustrates synthesis methods for embodiments of the present invention.
Figure 8:
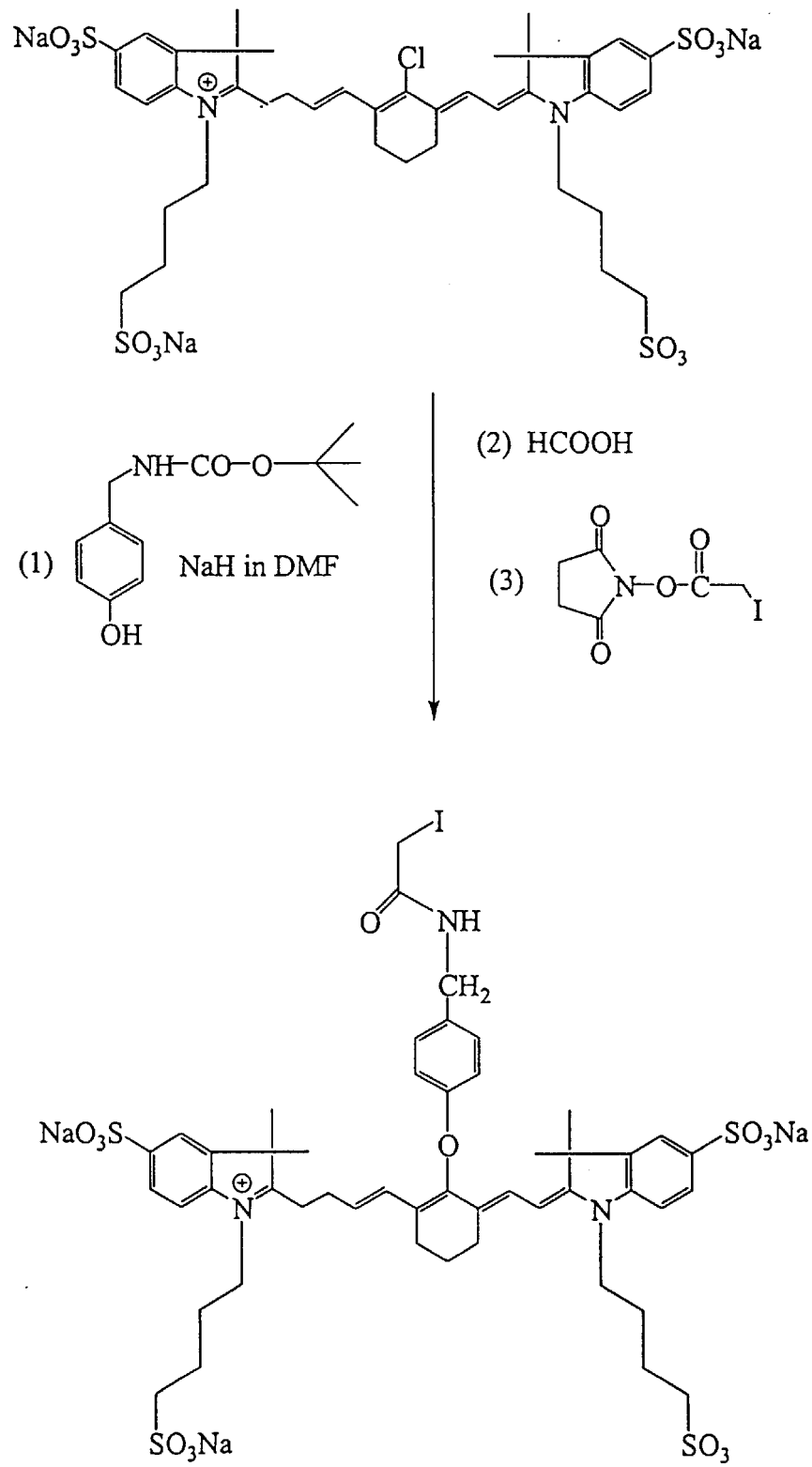
FIG. 8 illustrates synthesis methods for embodiments of the present invention.

C5 and C12 amino linker arms are attached to succinimidyl esters of both dyes and derivatized with iodoacetamide as illustrated in FIGS. 7 and 8. Coupling to dNTPγS is facile, since BODIPY-TR is commercially available from Molecular Probes as a thiol-reactive iodoacetamide with a C5 linker and can couple to thiophosphate oligonucleotides (see, Molecular Probes Inc., online catalog www.molecularprobes.com. and Hermanson, *Bioconjugate Techniques*, Academic Press, New York, 1996, 228.).

D. dUTPγS-Dye Synthesis

The iodoacetamide dyes are coupled to dUTPγS. The coupling conditions are as specified by Molecular Probes Inc. for conjugating iodoacetamide-activated dyes to phosphorothioate oligonucleotides. The synthesized compounds are tested as polymerase substrates.

Example 3

This Example illustrates the synthesis of DABCYL-dUTP-BODIPY TR (see, FIG. 9).

A. Preparation of DABCYL-sulfoNHS

DABCYL (108 mg, 0.4 mmole; Aldrich 25,019-8 Methyl red) was dissolved in a mixture of dry N,N-dimethylformamide (10 mL; Aldrich 22,705-6) and dry pyridine (96 mg, 1.2 mmole; Aldrich 27,097-0). N-Hydroxysulfosuccinimide (260 mg, 1.2 mmole; Pierce 24510) and N,N'-dicyclohexylcarbodiimide (250 mg, 1.2 mmole; Pierce 20320) were added and the mixture was stirred at 50° C. for 2 hours under a nitrogen atmosphere. The reaction was monitored by TLC (MKC18F Reversed Phase; Whatman 4803-110; developed in 0.1 M triethylammonium acetate, pH 7, 80% acetonitrile). After dilution with ether, the supernatant was decanted, the product was washed with ether on a filter, dried, and stored dessicated at −20° C.

B. Synthesis of DABCYL-dUTP

Aminoallyl-dUTP (10 mg, 20 μmole; Sigma A 0410) was mixed with DABCYL-sulfoNHS (30 mg, 30 μmole; from step A) in 3 mL of 0.1 M sodium carbonate pH 8.3. The mixture was incubated in the dark for 4 hours at room temperature and the reaction was monitored by TLC (as in step A). The DABCYL-dUTP product was purified by reversed-phase HPLC using a linear gradient from 0% to 100% of Buffer B mixed into Buffer A over 20 minutes (Buffer A is 0.1 M triethylammonium acetate in water, pH 7, 4% acetonitrile; Buffer B is the same as Buffer A with 80% acetonitrile).

C. Synthesis of DABCYL-dUTP-thiol

DABCYL-dUTP (9 mg, 12 μmole; from step B) was dissolved in 1 mL of 0.1 M MES pH 5.7 (Sigma M 3023) and adjusted to pH 5.75. Cystamine dihydrochloride (10 mg, 44 μmol; Sigma C 8707) was dissolved in 2.5 mL of 0.1 M MES pH 5.7 and adjusted to pH 5.75. EDC (9 mg, 47 μmol; Pierce 22980) was dissolved in 0.5 mL of 0.1 M MES pH 5.7 and was added immediately to the DABCYL-dUTP solution. After 10 minutes, the cystamine solution was added and the pH was maintained between 5.5 and 5.8 while the reaction proceeded at room temperature. After two hours, the pH was adjusted to 7.0 and the sample was stored at −20° C. The product was purified by reversed-phase HPLC as in step B.

D. Synthesis of DABCYL-dUTP-BODIPY TR

DABCYL-dUTP-thiol (2.5 mg, 3 μmole; from step C) was dissolved in 5.4 mL of 5 mM TCEP (Pierce 20490), 30 mM sodium phosphate adjusted to pH 7.5. BODIPY TR-iodoacetamide (5mg, 7.4 umol; Molecular Probes D-6011) was dissolved in 2.6 mL of N,N-dimethylformamide and was added to the DABCYL-dUTP-thiol solution. After standing at room temperature in the dark for 5 hours, the product was purified by reversed-phase HPLC as in step B.

E. Determination of Quenching Efficiency

The quenching efficiency of DABCYL-dUTP-BODIPY TR was determined as follows. First, the fluorescence of a sample containing the dye BODIPY TR is measured. Second, a sample containing the same concentration of the nucleotide triphosphate having a γ-phosphate with a fluorophore moiety attached i.e., DABCYL-dUTP-BODIPY TR is measured. Thereafter, the quenching efficiency, which is equal to $F_o-F/F_o$ wherein $F_o$ is fluorescence of the BODIPY TR alone and F is the fluorescence of DABCYL-dUTP-BODIPY TR is calculated. The fluorescence quenching efficiency of DABCYL-dUTP-BODIPY TR is at least 5 fold compared to the BODIPY TR alone.

All publications, patents and patent applications mentioned in this specification are herein incorporated by reference into the specification in their entirety for all purposes. Although the invention has been described with reference to preferred embodiments and examples thereof, the scope of the present invention is not limited only to those described embodiments. As will be apparent to persons skilled in the art, modifications and adaptations to the above-described invention can be made without departing from the spirit and scope of the invention, which is defined and circumscribed by the appended claims.

What is claimed is:

1. A heterogeneous assay method for detecting pyrophosphate cleavage, the components of the assay comprising a labeled NTP, a target nucleic acid, a primer nucleic acid and a polymerase, said method comprising:
    (a) flowing said labeled nucleotide triphosphate (NTP) having a γ-phosphate with a fluorophore moiety attached thereto, past an immobilized component selected from the group consisting of said polymerase and said target nucleic acid;
    (b) incorporating said NTP on a primer strand hybridized to said target nucleic acid using said polymerase and releasing said γ-phosphate with said fluorophore moiety attached thereto; and
    (c) detecting said fluorescent moiety thereby detecting pyrophosphate cleavage.

2. The method according to claim 1, wherein said nucleotide triphosphate (NTP) is a member selected from the group consisting of deoxyadenosine triphosphate, deoxycytosine triphosphate, deoxyguanosine triphosphate, deoxythymidine triphosphate, and deoxyuridine triphosphate.

3. The method according to claim 1, wherein said nucleotide triphosphate (NTP) is a member selected from the group consisting of adenosine triphosphate, cytosine triphosphate, guanosine triphosphate and uridine triphosphate.

4. The method according to claim 1, wherein each of said detection is based upon a change in either intensity measurement or fluorescent lifetime measurement.

5. The method according to claim 1, wherein said nucleotide triphosphate (NTP) is a plurality of nucleotide triphosphates (NTPs).

6. The method according to claim 1, wherein each of said plurality of nucleotide triphosphates (NTPs) has an indicator of identity.

7. The method according to claim 6, wherein said indicator of identity allows said plurality of NTPs to be distinguished from one another.

8. The method according to claim 1, wherein said polymerase is a member selected from the group consisting of a DNA polymerase, a DNA dependent RNA polymerase and a reverse transcriptase.

9. The method according to claim 8, wherein said polymerase is a DNA polymerase.

10. The method according to claim 1, wherein said polymerase is immobilized on a solid support.

11. The method according to claim 1, wherein said target nucleic acid is immobilized on a solid support.

12. The method according to claim 11, wherein said solid support is a member selected from the group consisting of controlled pore glass, a glass plate, polystyrene, an avidin coated polystyrene bead, cellulose, nylon, acrylamide gel and activated dextran.

13. The method according to claim 1, wherein said assay is part of an integrated system for high-throughput DNA sequencing.

14. An assay method for detecting pyrophosphate cleavage, the components of the assay comprising a labeled NTP, a target nucleic acid, a primer nucleic acid and a polymerase, said method comprising:
    (a) flowing said labeled nucleotide triphosphate (NTP) having a γ-phosphate with a fluorophore moiety attached thereto, past an immobilized component selected from the group consisting of said polymerase and said target nucleic acid;
    (b) incorporating said NTP on a primer strand hybridized to said target nucleic acid using said polymerase and releasing said γ-phosphate with said fluorophore moiety attached thereto; and (c) detecting said fluorescent moiety thereby detecting pyrophosphate cleavage.

15. The method according to claim 14, wherein said nucleotide triphosphate (NTP) is a member selected from the group consisting of deoxyadenosine triphosphate, deoxycytosine triphosphate, deoxyguanosine triphosphate, deoxythymidine triphosphate, and deoxyuridine triphosphate.

16. The method according to claim 14, wherein said nucleotide triphosphate (NTP) is a member selected from the group consisting of adenosine triphosphate, cytosine triphosphate, guanosine triphosphate and uridine triphosphate.

17. The method according to claim 14, wherein each of said plurality of fluorescent species is detected based upon a change in either intensity measurement or fluorescent lifetime measurement.

18. The method according to claim 14, wherein said nucleotide triphosphate (NTP) is a plurality of nucleotide triphosphates (NTPs).

19. The method according to claim 14, wherein each of said plurality of nucleotide triphosphates (NTPs) has an indicator of identity.

20. A method for sequencing a target nucleic acid using an assay method for detecting pyrophosphate cleavage, the components of the assay comprising a labeled NTP, a target nucleic acid, a primer nucleic acid and a polymerase, said method comprising:

(a) providing said labeled nucleotide triphosphate (NTP) having a γ-phosphate with a fluorophore moiety attached thereto, and an immobilized component selected from the group consisting of said polymerase and said target nucleic acid;

(b) incorporating said NTP on said primer strand hybridized to said target nucleic acid using said polymerase and releasing said γ-phosphate with said fluorophore moiety attached thereto; and (c) detecting said fluorescent moiety by detecting pyrophosphate cleavage, thereby sequencing said target nucleic acid.

21. The method according to claim 20, wherein said polymerase is a DNA polymerase.

22. The method according to claim 20, wherein said polymerase is immobilized on a solid support.

23. The method according to claim 20, wherein said target nucleic acid is immobilized on a solid support.

24. The method according to claim 23, wherein said solid support is a member selected from the group consisting of controlled pore glass, a glass plate, polystyrene, an avidin coated polystyrene bead, cellulose, nylon, acrylamide gel and activated dextran.

25. The method according to claim 20, wherein said assay is part of an integrated system for high-throughput DNA sequencing.

* * * * *